United States Patent [19]
Wright et al.

[11] Patent Number: 5,213,809
[45] Date of Patent: May 25, 1993

[54] DELIVERY SYSTEM COMPRISING MEANS FOR CONTROLLING INTERNAL PRESSURE

[75] Inventors: Jeremy C. Wright; James B. Eckenhoff, both of Los Altos; Frederick H. Maruyama, San Jose; John R. Peery, Palo Alto, all of Calif.

[73] Assignee: ALZA Corporation, Palo Alto, Calif.

[21] Appl. No.: 849,848

[22] Filed: Mar. 12, 1992

Related U.S. Application Data

[63] Continuation of Ser. No. 469,861, Jan. 24, 1990, abandoned.

[51] Int. Cl.⁵ .............................................. A61K 9/24
[52] U.S. Cl. .................................... 424/473; 424/438; 604/892.1
[58] Field of Search ................... 424/473, 438; 604/892.1

[56] References Cited

U.S. PATENT DOCUMENTS

| | | | |
|---|---|---|---|
| 3,995,632 | 12/1976 | Nakano et al. | 128/260 |
| 4,564,363 | 1/1986 | Bagnall et al. | 604/891 |
| 4,595,583 | 6/1986 | Eckenhoff et al. | 424/15 |
| 4,612,186 | 9/1986 | Eckenhoff et al. | 424/15 |
| 4,643,731 | 2/1987 | Eckenhoff | 604/892 |
| 4,663,148 | 5/1987 | Eckenhoff et al. | 424/454 |
| 4,678,467 | 7/1987 | Eckenhoff et al. | 604/892 |
| 4,692,326 | 9/1987 | Eckenhoff et al. | 424/473 |
| 4,704,118 | 11/1987 | Eckenhoff | 604/892 |
| 4,716,031 | 12/1987 | Eckenhoff | 424/453 |
| 4,729,793 | 3/1988 | Eckenhoff et al. | 106/169 |
| 4,772,474 | 9/1988 | Eckenhoff et al. | 424/465 |
| 4,800,056 | 1/1989 | Eckenhoff et al. | 264/129 |
| 4,814,180 | 3/1989 | Eckenhoff et al. | 424/473 |
| 4,872,873 | 10/1989 | Zingerman | 604/892.1 |
| 4,876,093 | 10/1989 | Theeuwes et al. | 424/438 |
| 4,968,508 | 11/1990 | Oren | 424/468 |
| 5,000,957 | 3/1991 | Eckenhoff | 424/438 |
| 5,045,082 | 9/1991 | Ayer | 604/892.1 |

FOREIGN PATENT DOCUMENTS 031043 6/1989 European Pat. Off. .

*Primary Examiner*—Thurman K. Page
*Assistant Examiner*—D. Gabrielle Phelan
*Attorney, Agent, or Firm*—Jacqueline S. Larson; Paul L. Sabatine; Edward L. Mandell

[57] ABSTRACT

A dispensing device is disclosed for delivering a beneficial agent. The device comprises (1) a semipermeable housing defining a internal space, (2) an optional and presently preferred in the space, (3) a heat responsive composition comprising a beneficial agent in the space, (4) a space consuming member in the device, (5) a nontoxic compound blended with the heat responsive composition for enhancing its viscosity; (6) an exit port in the wall for increasing the internal pressure of the dispenser and for simultaneously letting the beneficial agent exit through said port from the device, and (7) an embodiment comprising a prehydrating fluid for fastening the start-up of delivery from the delivery system.

20 Claims, 10 Drawing Sheets

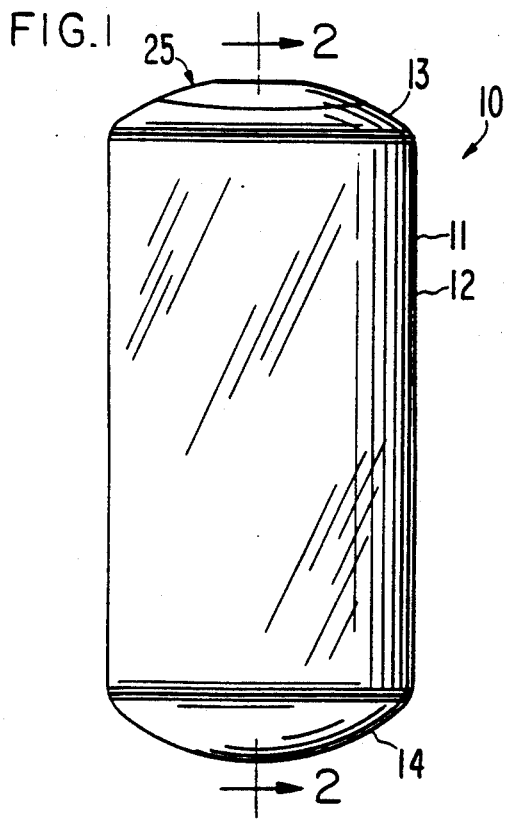
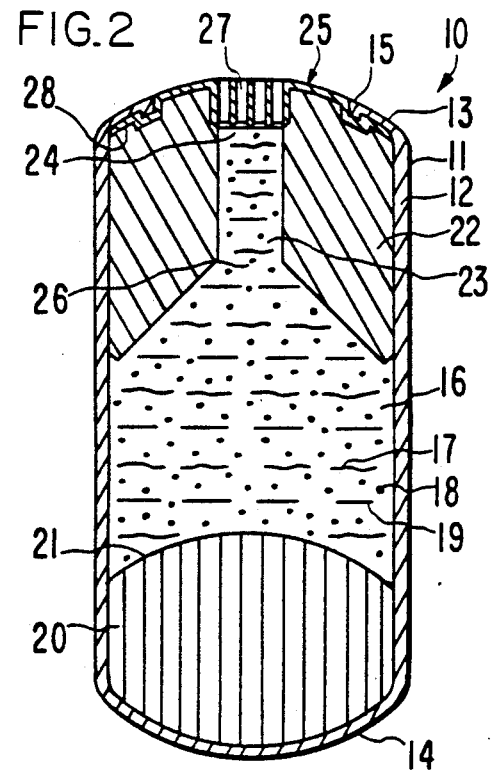
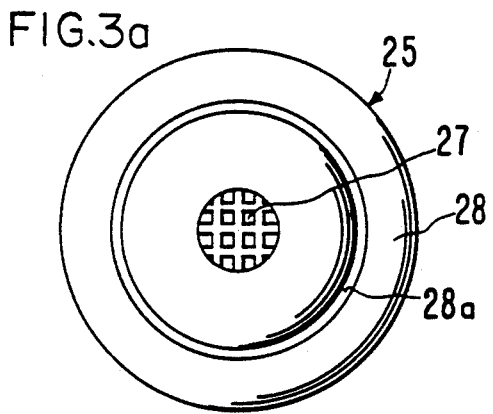
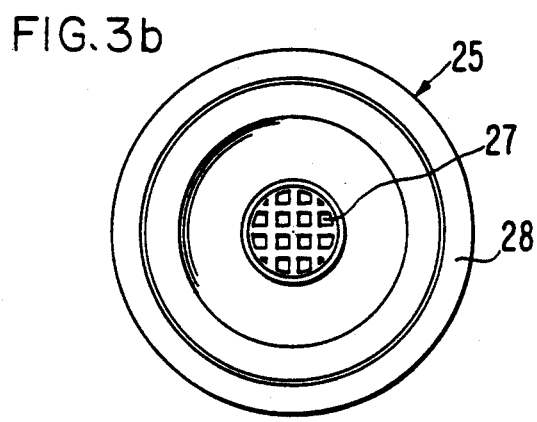
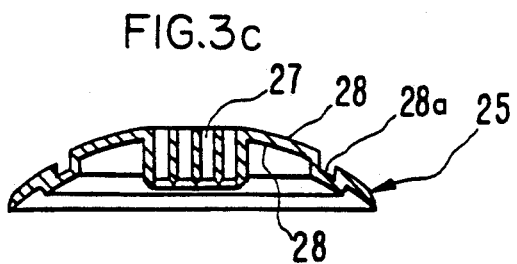

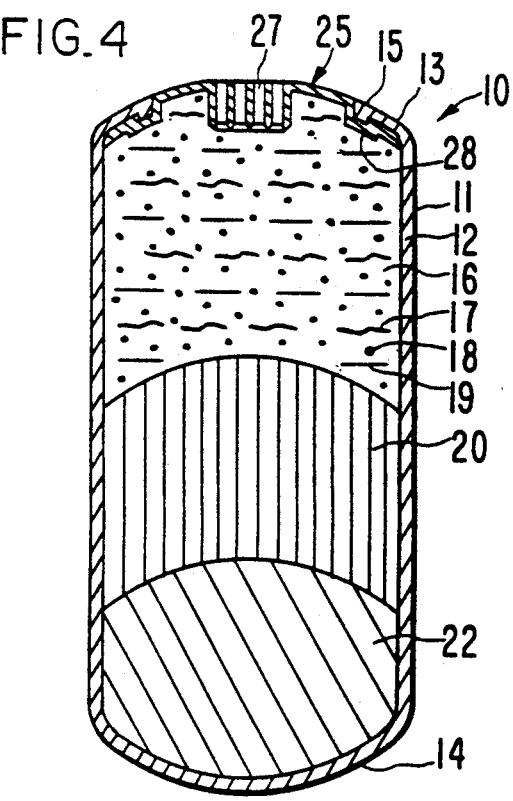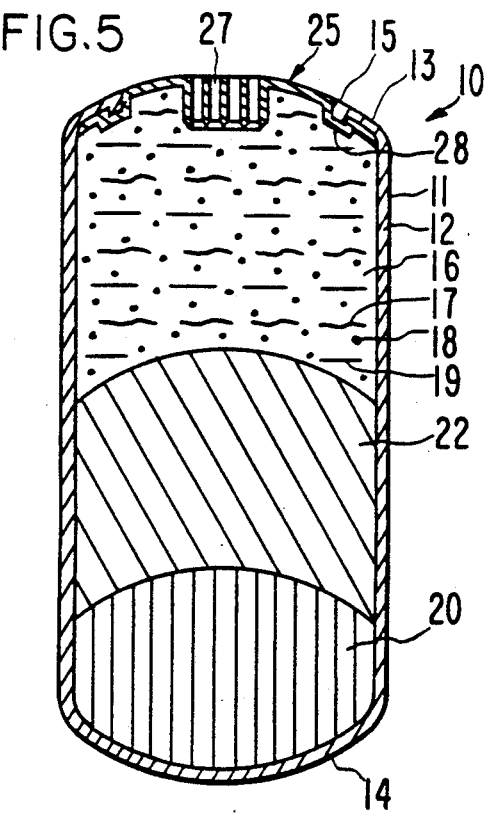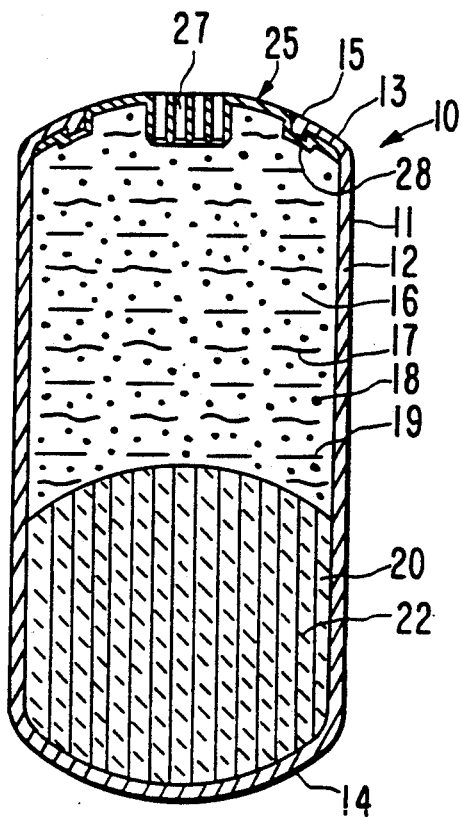

ated under 35 U.S.C. section 120.

DELIVERY SYSTEM COMPRISING MEANS FOR CONTROLLING INTERNAL PRESSURE

This application is a continuation of application Ser. No. 07/469,861, filed Jan. 24, 1990, now abandoned, and benefit of the filing date of said earlier filed application is claimed under 35 U.S.C. section 120.

DISCLOSURE OF TECHNICAL FIELD

This invention pertains to both a novel and useful delivery system. More particularly, the invention relates to an improvement in a delivery system wherein the system comprises a wall that surrounds an internal lumen comprising a thermo-responsive beneficial agent formulation, an expandable driving member, and an optional density member, and wherein the improvement comprises means for governing the internal pressure of the delivery system, and means for increasing the thermo-responsive formulation's viscosity. An embodiment of the invention concerns prehydrating the delivery system as a means for advancing the beginning of drug delivery from the delivery system.

DISCLOSURE OF BACKGROUND ART

Delivery systems for dispensing a beneficial agent to a biological environment of use are known to the prior art. For example, delivery systems comprising a wall that surrounds an internal lumen that houses a thermo-responsive formulation, an expandable driving member and a density member are known in U.S. Pat. Nos. 4,595,583; 4,612,186; 4,624,945; 4,684,524; 4,692,336; 4,717,566; 4,717,568; 4,717,718; 4,772,474; and 4,844,984 all issued to Eckenhoff, Cortese and Landrau, in U.S. Pat. Nos. 4,663,148; 4,663,149; 4,678,467; 4,716,013; 4,781,714; 4,800,056; and 4,814,180 issued to Eckenhoff, Theeuwes, and Deters, and in U.S. Pat. Nos. 4,675,174 and 4,704,118 issued to Eckenhoff. These dispensing systems of the prior art are extraordinarily effective for delivering beneficial agents that are hydrophilic, hydrophobic, lipophilic or lipophobic to a biological environment of use. The delivery systems operate successfully for their intended use, and they can deliver numerous difficult to deliver beneficial agents at a controlled and predictable rate. Sometime, however, the delivery systems, when in operation in a biological environment of use having a high pressure or high partial pressures of biological gases, exhibit a delivery rate that is unpredictable. This is due to a low internal pressure of a gas phase in the delivery system relative to an exterior higher pressure or partial pressure. It has now been unexpectedly found that the delivery behavior of these delivery systems can be improved, (1) by providing a means for increasing the interior pressure to overcome an unpredictable delivery behavior associated with an interior low pressure, and (2) by providing a means for increasing the viscosity of the thermo-responsive formulation inside the delivery system. It has also been unexpectedly found the delivery system can be improved, (3) by prehydrating the delivery system for shortening the time needed for the delivery system to start delivering a beneficial agent.

DISCLOSURE OF OBJECTS OF THE INVENTION

Accordingly, it is a principle object of this invention to provide a novel and useful delivery system that overcomes the disadvantages associated with the prior art.

Another object of the present invention is to provide an improvement in a delivery system comprising means for establishing a high internal pressure inside a delivery system thereby providing a controlled and predictable delivery behavior over time for the delivery system.

Another object of the present invention is to provide an improvement in a delivery system comprising a means for increasing the viscosity and/or yield stress of a thermo-responsive formulation inside the delivery system that cooperates with a means for increasing the internal pressure to produce a controlled and known delivery behavior over a prolonged period of time.

Another object of the present invention is to provide a delivery system comprising an internal pressure substantially equal to or greater than its external pressure, and which delivery system delivers a beneficial agent at a rate controlled by the delivery system that is substantially independent of the exterior pressure.

Another object of the present invention is to provide a delivery system comprising an exit port that increases the internal hydraulic resistance to flow from the delivery system.

Another object of the present invention is to provide a delivery system comprising a greater inside pressure relative to the outside pressure for compressing inside void volume and for decreasing void volume that is gas-filled and that formed during manufacture of a flowable beneficial agent formulation.

Another object of the present invention is to provide a delivery system that delivers a beneficial agent at a more consistent and predictable rate in the widely varying conditions of a biological environment.

Another object of the invention is to provide a therapeutic delivery system for use in ruminants that delivers a medicine, a nutrient, or a biocide at a controlled rate over time and which delivery system compensates for variations in the biological ruminant's environment during delivery from the delivery system.

Another object of the invention is to provide a therapeutic delivery system that can remain in the rumen of a ruminant for a prolonged period of time substantially free of adverse influences of the rumen.

Another object of the invention is to provide a delivery system manufactured in the form of a drug dispensing device that is self-contained, self-starting, and self-powered in a fluid environment, is easy to use, and can be manufactured at a lesser cost thereby increasing the usefulness of the dispensing device particularly for treating domestic and zoo animals.

Another object of the invention is to provide a delivery system comprising a temperature-sensitive composition, an expandable driving member, a densifier, and an exit port, which exit port operates to increase the internal pressure of the delivery system in reference to the external pressure.

Another object of the present invention is to provide a drug delivery device comprising a semipermeable wall that surrounds in at least a part of an internal lumen and contains a thermo-sensitive composition comprising a compound that increases the viscosity and/or yield stress of the composition, and which thermo-sensitive composition contains a beneficial agent and is delivered by the combined physical-chemical operations of the composition melting and becoming semisolid to fluid or the like, with the composition displaced through an exit port that offers resistance to flow, thereby substantially preventing and lessening a premature delivery from the device.

Another object of the invention is to provide a drug delivery system comprising a dense member for keeping the delivery system in the rumen over time, wherein the delivery system administers composition that is a complete pharmaceutical dosage regimen for a prolonged period of time, the use of which delivery system requires intervention only for the initiation of the regimen.

Another object of the invention is to provide a drug delivery system that can deliver a beneficial drug contained in a thermo-responsive, lipophilic pharmaceutically acceptable carrier comprising an inert compound that increases the viscosity and/or yield stress of the carrier, and which carrier melts in the rumen in the presence of thermal energy absorbed from the rumen and thereby is converted into a dispensable composition that is innocuous for substantially avoiding mammalian tissue irritation and interaction with mammalian protein tissue.

Another object of the invention is to provide a delivery comprising a housing containing a thermo-responsive hydrophilic or hydrophobic composition comprising insoluble to soluble drugs, and which thermo-responsive composition in response to energy input present in the gastrointestinal tract of a ruminant, changes its form and becomes dispensable for operative delivery through an exit port comprising a plurality of passageways for increasing the resistance to flow of the thermo-responsive composition.

Another object of the invention is to provide a drug delivery system for dispensing a drug to a ruminant, which delivery system comprises a thermoplastic wall that surrounds a lumen comprising a thermo-responsive, non-aqueous composition, a dense member, and an expandable component, and which delivery system comprises a dispensing head that increases the internal pressure to lessen gap formation for decreasing aberrant pumping behavior from the delivery system.

Another object of the invention is to provide a delivery system that is prehydrated with a pharmaceutically acceptable fluid to provide an early start of beneficial agent form the delivery system.

Another object of the invention is to provide substantially immediate beneficial agent to an animal by prehydrating the delivery system to overcome the time required for fluid to be imbibed into the delivery system.

Other objects, features of the invention will be more apparent to those skilled in the dispensing art from the following detailed description of the specification, taken in conjunction with the drawings and the accompanying claims.

BRIEF DESCRIPTION OF DRAWING FIGURES

In the drawing figures, which are not drawn to scale but are set forth to illustrate various embodiments of the invention, the drawing figures are as follows:

FIG. 1 is a view of a delivery system designed and manufactured for administering orally a beneficial agent to a warm blooded animal;

FIG. 2 is an opened view of the delivery system of FIG. 1, through 2—2 of the vertical length of the delivery system for illustrating the structure of the delivery system comprising a wall, a thermo-responsive composition, an expandable member, a dense member, and an exit port for increasing the internal pressure of the delivery system;

FIGS. 3a, 3b and 3c illustrate the exit port of the delivery system seen in FIG. 2, with 3a depicting a top view, FIG. 3b a bottom view, and FIG. 3c a cross-sectional view of the exit port;

FIG. 4 is an opened view of the delivery system of FIG. 1 for illustrating another embodiment of the delivery system comprising a different internal arrangement of the components of the delivery system;

FIG. 5 is an opened view of the delivery system depicting a semipermeable wall that surrounds a lumen comprising a different positioning of the internal parts that act in concert for the controlled delivery of a beneficial agent over time;

FIG. 6 is a cross-section of the delivery system illustrating an expandable member comprising a density member dispersed therein;

In the drawings and in the specification, like parts in related figures are identified by like numbers. The terms appearing earlier in the specification and in the description of the drawings, as well as embodiments thereof, are further detailed elsewhere in the disclosure.

DETAILED DISCLOSURE OF THE DRAWINGS

Figure 7:
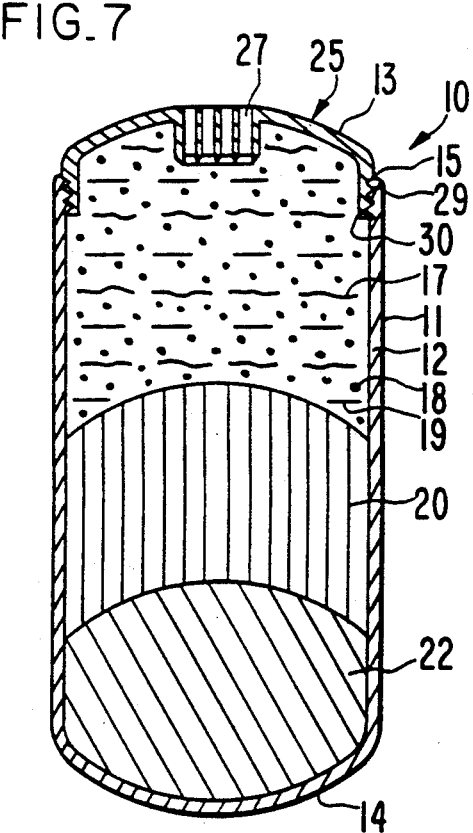
FIG. 7 is an opened view of a delivery system provided by the invention wherein the delivery system comprises a screw-like arrangement for releasably attaching an internal pressure-producing head to the body of a delivery system.

Turning now to the drawing figures in detail, which are examples of new and useful therapeutic delivery systems for dispensing a beneficial agent, and which examples are not to be construed as limiting, one example of a delivery system is depicted in FIG. 1 identified by the numeral 10. In FIG. 1, delivery system 10 is manufactured as a dispenser comprising a body 11 formed by a wall 12 that surrounds an internal lumen, not seen in FIG. 1. Delivery system 10 comprises a lead end 13 for receiving an exit member, not seen in FIG. 1, and a trailing end 14.

Drawing FIG. 2 depicts an opened section the therapeutic dispensing system 10 of FIG. 1 through 2—2 of FIG. 1. Therapeutic system 10 of FIG. 2 comprises body 11, wall 12, lead end 13, rear end 14, and opening 15 in wall 12. Wall 12 surrounds an internal lumen or compartment 16. Wall 12 comprises in a presently preferred embodiment in at least a part, a semipermeable wall forming composition that is substantially permeable to the passage of an external fluid, and it is substantially impermeable to the passage of a beneficial agent and other ingredients contained in delivery system 10. In another embodiment wall 12 comprises at least in part a semipermeable composition with the remainder of the wall comprising a different composition substantially impermeable to the passage of fluid and substantially impermeable to the passage of a beneficial agent. Wall 12 is non-toxic and it maintains its physical and chemical integrity, that is, it doesn't erode during the dispensing period. System 10, in a presently preferred embodiment, is manufactured with wall 12 as a single unit member, by injection molding, or the like.

Lumen 16 contains a thermo-responsive heat sensitive composition 17, identified by wavy lines, a beneficial agent 18, represented by dots, and an inert compound 19, represented by dashes, for increasing the viscosity or the internal resistance to flow of thermo-responsive composition 17. Lumen 1 further contains an expandable driving member 20 that is in layered contact with a contacting surface 21 of thermo-responsive composition 17. Both the thermo-responsive composition 17 and the expandable member 20 have a shape that corresponds to the internal shape of lumen 16. Lumen 16 also contains a dense member or densifier 22 that is in contact with thermo-responsive composition 17, which dense member 22 is positioned in lumen 16 distant from expandable member 20. Dense member 22 comprises a passageway or bore 23 with an opening 24 adapted for receiving in tight relationship an exit member 25, which exit member 25 is used for increasing the internal hydraulic resistance to flow of thermo-responsive composition 17. Dense member 22 comprises an opening 26 for letting thermo-responsive composition 17 flow from lumen 16 to exit member 25 and hence to the exterior of delivery system 10. Dense member 22 is a component of delivery system 10 designed for keeping system 10 in the rumen of an animal over a prolonged period of time.

FIGS. 3a, 3b and 3c illustrate one presently preferred embodiment of exit member 25. FIG. 3a is a top view of exit member 25 depicting a plurality of tiny passageways 27 surrounded by a supporting shoulder 28. Shoulder 28 receives wall 12 in a curved shoulder relation to keep exit member 25 firmly inside lumen 16. FIG. 3b is a bottom view of exit member 25 which view depicts an array of parallel passageways 27 sized to produce a pressure difference across exit member 25 seen in a screen-like arrangement, and support by the perimeter shoulder of exit member 25. In FIG. 3a, the bottom of the shoulder also is identified by the numeral 28. FIG. 3c is a cross-section through exit member 25 for illustrating a plurality of passageways 27. In cross-section, the passageways can be circular, square, hexagonal or any appropriate shape that increases the resistance to flow of the thermo-responsive composition 17 from delivery system 10. In section, the passageways 27 can be any shape that is appropriate for economy of manufacturing or structural strength required by a plurality of passageways consistent with space and materials. In FIG. 3c, exit member 25 comprises a shoulder, or perimeter that extends around passageways 27 and it comprises a wall 12 receiving indentation 28a for releasably receiving and for fixing exit member 25 to wall 12 of delivery system 10, which prevents exit member 25 from separating from delivery system 10 during operation of the delivery system.

Exit member 25, as seen in FIGS. 3a, 3b and 3c, is provided by the invention to establish a state of high internal back pressure inside the delivery system through the design of the exit member coupled with the physical properties of the thermo-responsive composition. A high internal pressure operates to keep any possible voids in the system from expanding due to gas passing into the delivery system from a surrounding ruminal environment. A large volume of gas is produced during feeding by a ruminant. The ruminants have four stomach compartments, and the rumen is the largest of the four stomach compartments. In ruminants, ingested feed first passes into the rumen, where it is pre-digested or degraded by fermentation. During this period of fermentation, the ingested feed may be regurgitated to the mouth for salivation and mastication. Also, gases are produced during this normal process of digestion of feed. The ruminal gas composition usually comprises 40 to 70% carbon dioxide, 20 to 40% methane, 15 to 35% nitrogen, 0.1 to 0.7% oxygen, 0.1 to 0.5% hydrogen and 0.01 to 0.05% hydrogen sulfide. The rumen temperature is maintained at a relatively constant 38 to 42 degrees C. during fermentation, and copious salivary secretions of bicarbonate and phosphate buffer the rumen fermentations usually to a pH of between 5 to 7. The total pressure in the rumen ranges from slightly below 760 mm Hg to 830 mm Hg absolute. After salivation and mastication, the partially digested feed is re-swallowed and ultimately finds its way through the rumen and reticulum to the omasum and abomasum of the stomach for passage through the remainder of the animal's alimentary canal during which assimilation of the available food products occurs. The composition of rumen gas is disclosed in *Canadian Journal of Animal Science* Vol. 41, pp 187-96, (1961): and in *The Physiology of Domestic Animals* 7th Ed., pp 382-84, (1955), published by Comstock Publishing Associates.

In operation, gases present in the ruminal environment diffuse through the semipermeable wall into the lumen and diffuse into any existing voids in the delivery system The voids can be unavoidably manufactured into the delivery system during manufacture of the expandable member, the density member, and filling of the partition and drug formulation layers and they can row in size if the partial pressure of gas components in the void is less than the partial pressure of gas components in the surrounding environment. The gases from the permeant wall diffuse down the activity gradient into the void to reach equilibrium. Further, the severity of this problem is magnified by the fact that several ruminal gases diffuse through semipermeable walls at much greater rates than the air in the voids. If the pressure surrounding the void is high, the tendency of external gases to diffuse into the void and expand will be greatly reduced, the void will not grow and it will be squeezed into a relatively incompressible state. This invention by increasing the internal pressure relative to the external pressure overcomes and eliminates erratic pumping rates and premature delivery attributed to void volume.

FIG. 4 depicts another manufacture of delivery system 10 as seen in opened section. Delivery system 10 comprises body 11, wall 12, lead end 13, rear end 14, and opening 15 in wall 12. Wall 12 surrounds lumen 16. Lumen 16 contains a thermo-responsive composition 17, a beneficial agent 18, and an inert compound 19 which increases the viscosity and/or yield stress of thermo-responsive composition 17. Lumen 16 also contains a dense member 22 and an expandable member 20. Delivery system 10 comprises in lead end 13 an exit member 25. Exit member 25 comprises a plurality of exit passageways 27 for releasing under pressure thermo-responsive composition 17 from lumen 16. Exit member 25 comprises a shoulder 28 that extends around the passageways 27, with wall 12 overlapping onto shoulder 28 to keep exit member 25 positioned in opening 15 in wall 12. Exit member 25 functions to enhance the interior pressure relative to the outside pressure during operation of the delivery system, thereby (1) compressing any evolved gas voids and decreasing the void volume in a flowable thermo-responsive composition, (2) supporting the wall internally against collapsing external forces, (3) substantially prevent diffusional and turbulent mixing of ruminal fluid contents with the thermo-responsive composition in the delivery system, (4) prevents, effectuates and restricts a premature discharge of a thermo-responsive composition from within the delivery system due to pressure developed within by gas evolution or temperature changes in storage or in transport, and (5) makes the delivery performance of delivery system 10 more consistent and predictable under the widely varying biological conditions of the ruminant.

The delivery system provides a consistent and predictable release rate pattern of beneficial agent delivery as seen by the following equation (for exit member passageways of circular cross section):

$$\Delta P = \frac{Q(8 \mu L)}{n \pi R^4}$$

wherein $\Delta P$ is the pressure drop across the exit port, Q is the volumetric release rate, $\mu$ is the viscosity of the thermo-responsive composition, L is the length of the exit port, n is the number of exit passageways and R is the radius of the exit passageways. For example, $\Delta P$ for a delivery system provided by the equation should exceed 4 psi and preferably in the range of 6 to 50 psi to substantially lessen erratic pumping and premature delivery. The number of exit passageways can be greater than or equal to 1. Generally, for example, when a grid like exit member is used, the number of exit passageways is between 1 to 50, and the radius of the exit passageways are then adjusted so that the pressure drop is in the desired range.

FIG. 5 depicts another manufacture of delivery system 10 provided by the invention. Delivery system 10 comprises body 11, wall 12, lead end 13, rear end 14, opening 15, lumen 16, thermo-responsive composition 17, beneficial agent 18, inert compound 19, dense member 22, expandable member 20, exit member 25, passageways 27 and shoulder 28. In the manufacture depicted, passageways 27 comprise capillaries or small tubes in slender elongated form comprising a small bore and held in spaced apart order by exit member 25. In FIG. 5, the density member is positioned between thermo-responsive composition 17 and expandable member 20.

FIG. 6 depicts another manufacture provided by the invention. The delivery system 10 provided by the invention in this manufacture comprises a body 11, wall 12, lead end 13, rear end 14, opening 15, lumen 16, thermo-responsive composition 17, beneficial agent 18, inert compound 19, exit member 25, passageways 27 and shoulder 28. In FIG. 6, expandable member 20 comprises a dense member 22 dispersed throughout expandable member 20. In FIG. 6, exit member 25 and inert compound 19 operate in combination to produce and regulate the internal pressure in delivery system 10.

FIG. 7, depicts another manufacture provided by the invention. In FIG. 7, delivery system 10 comprises a body 11, a wall 12, lead end 13, rear end 14 opening 15, lumen 16, thermo-responsive composition 17, beneficial agent 18, inert compound 19, displacement member 20 and dense member 22. In FIG. 7 delivery system 10 is made with threads 29 at the top of wall 12 for turning threads 30 of exit member 25 into the delivery system. The mated threads act as a retaining means for releasably holding exit member 25 in delivery system 10. In this manufacture, delivery system 10 can be recovered, the exit member turned therefrom and delivery system 10 refilled for multiple use. In one embodiment in FIG. 7, the improvement comprises exit means 25 for governing the internal pressure of delivery system 10 coupled with viscosity means 19 for increasing the thermo-responsive formulation's viscosity.

Figure 8:
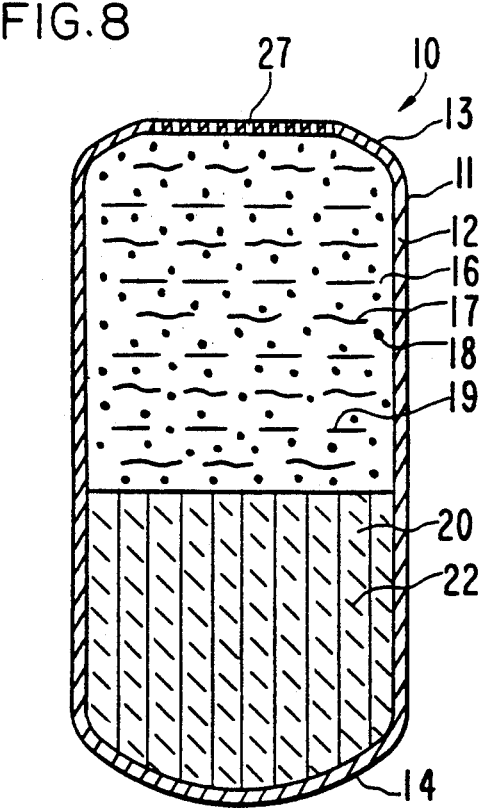
FIG. 8 is an opened view of a delivery system provided by the invention wherein the delivery system comprises a plurality of exit ports formed in the wall of the delivery system, which exit ports are designed for maintaining a high internal pressure inside the delivery system.

FIG. 8 depicts another delivery system 10 provided by the invention. In FIG. 8, delivery system 10 comprises a body 11, a wall 12, lead end 13, rear end 14, lumen 16 comprising a thermo-responsive composition 17 containing beneficial agent 18 and inert viscosity compound 19. In FIG. 8, delivery system 10 comprises a displacement member 20 consisting of an osmagent that imbibes and absorbs fluid through wall 12 to form a solution that continuously fills lumen 16 and thereby displaces thermo-responsive composition 17 from delivery system 10. Displacement member 20 comprises a densifier 22 for keeping delivery system 10 in the ruminant for a prolonged period of time. In FIG. 8, delivery system 10 comprises a multiplicity of exit passageways 27 integrally formed in wall 12 as an integral exit member 25 for increasing the resistance to flow of thermo-responsive composition 17 from delivery system 10, and concomitantly increasing the internal pressure inside delivery system 10.

Figure 9:
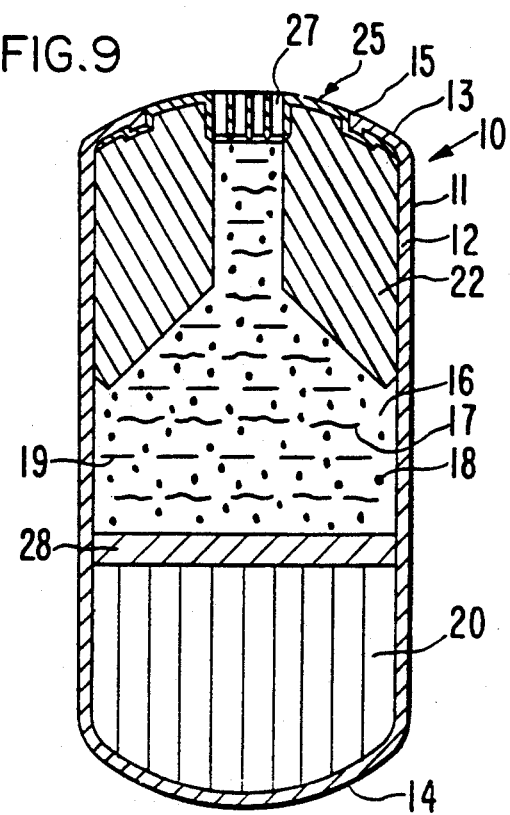
FIG. 9 is an opened view of the delivery system provided by the invention wherein the delivery system comprises an internal layer for increasing the efficiency of the delivery system.

FIG. 9 illustrates another delivery system 10 provided by the invention. In FIG. 9, delivery system 10 comprises a body 11, a wall 12, lead end 13, rear end 14, opening 15, internal lumen 16 thermo-responsive composition 17, beneficial agent 18, inert compound 19, displacement member 20 and a dense member 22. In FIG. 9, thermo-responsive composition 17 is separated from expandable member 20 by a lamina or layer 28. Layer 28 is positioned between the active thermo-formulation 17 and the expandable member 20 for substantially reducing diffusion, migration, entrapment, or the like of active agent 18 in expandable member 20. Layer 28 also protects the active agent formulation from any possible interaction with the expandable member, thereby improving the stability of the active agent formulation. In one presently preferred embodiment, layer 28 is made from a soft or a flexible polymeric composition for aiding in pushing the maximum amount of formulation 17 containing agent 18 from delivery system 10. Thus, layer 28 serves as a means for increasing the delivery efficiency of delivery system 10 by insuring the total force generated by expandable member 20 is applied against heat-responsive formulation 17, agent 18, for squeezing formulation 17 through exit pressure inducing passageways 27. Layer 28 in operation functions like a piston, and it is so constructed to movably provide and maintain a tight piston-head arrangement between the active agent phase and the expandable phase in lumen 16. Layer 28 is frictionally disposed, but it is free to move within delivery system 10 by sliding, while at the same time maintaining the operability of delivery system 10. Layer 28 preferably comprises nontoxic materials.

Figure 10:
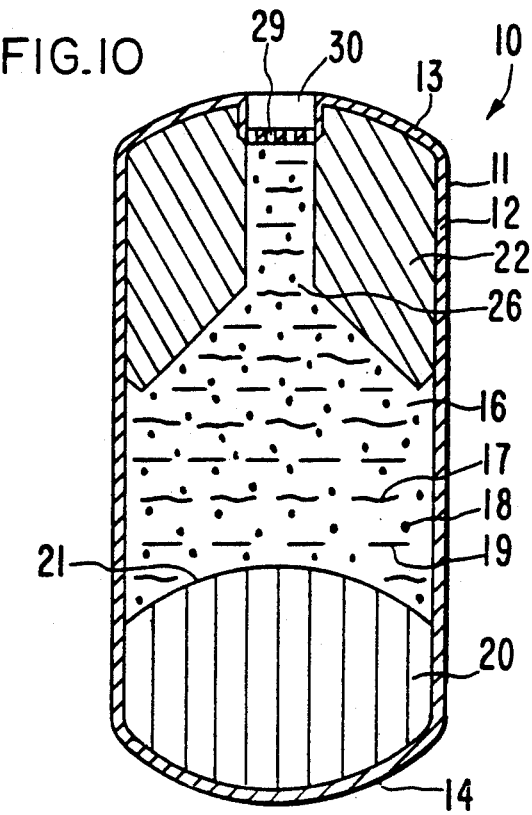
FIG. 10 is an opened sectional delivery system depicting the delivery system comprising means comprising a plurality of capillary like passageways in a retaining member releasably held in the delivery system.

FIG. 10 illustrates another delivery system 10 seen in opened section as provided by this invention. In FIG. 10, delivery system 10 comprises a body 11, a wall 12, lead end 13, rear end 14, density member 22, push displacement member 20, aperture 26 extending through density member 22, interface 21, and lumen 16 comprising a thermo-responsive composition 17 comprising beneficial agent 18 and inert viscosity enhancing agent 19. In FIG. 10, delivery system 10 comprises a plurality of passageways 29 optionally designed as a releasable perforated plate, a perforated or ridged plastic or metal plate, or a plurality of capillaries for elevating the pressure inside dosage system 10. The capillaries in one manufacture comprise a number of slender elongated tubes comprising a very small bore for decreasing the flow rate from delivery system 10. A passageway retaining member 30 releasably holds passageway inducing pressure member 29 in delivery system 10 during the beneficial agent 18 releasing period.

Figure 11:
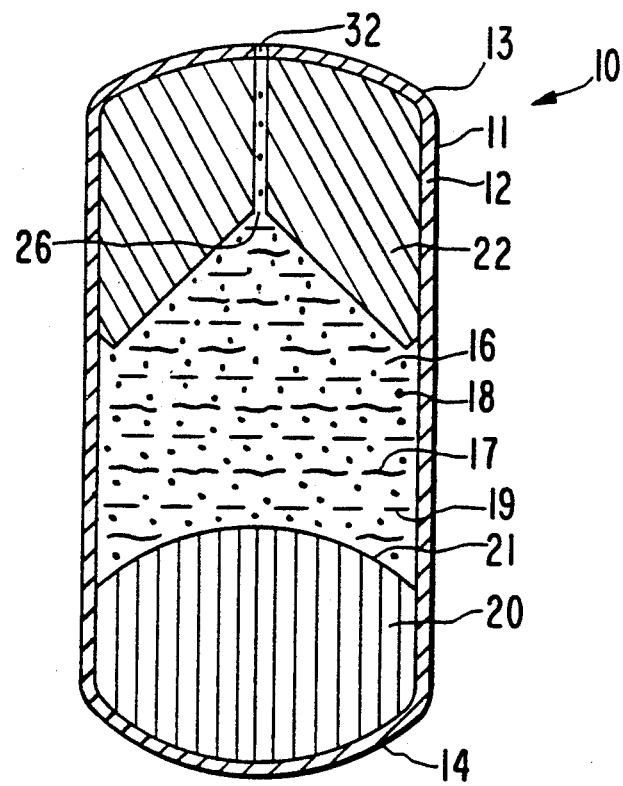
FIG. 11 is a cross-section view of a delivery system comprising a single exit designed for maintaining an internal back pressure inside the delivery system.

FIG. 11 illustrates another delivery system 10 seen in opened section as provided by this invention. In FIG. 11, delivery system 10 comprises a body 11, a wall 12, lead end 13, rear end 14, density member 22, push displacement member 20, aperture 26 entering into capillary 32 of density member 22, interface 21, and lumen 16 comprising thermo-responsive composition 17 comprising beneficial agent 18 and inert viscosity enhancing agent 19. In FIG. 11, delivery system 10 comprises a single passageway 32 for (a) increasing the internal pressure of delivery system 10, for (b) restricting drug flow from delivery system 10 and for (c) acting simultaneously with inert viscosity enhancing agent 19 for restricting drug flow from delivery system 10. FIG. 11 depicts an optional embodiment comprising a single exit passageway. A single passageway can be used with the proviso that its cross-sectional area functions as a means for pressurizing lumen 16 of delivery system 10 and as a means for controlling the flow rate of beneficial agent 18 from lumen 16.

The rumen-retentive delivery system 10 as provided by the invention can be manufactured in a variety of sizes and shapes for use with ruminant animals. One presently preferred shape is a cylinder-like shape. For example, for use with sheep, delivery system 10 can embrace a capsule-like shape comprising a diameter of about 0.5 inches to 1 inch (1.3 cm to 2.5 cm) and a length of about 0.5 inches to 2.5 inches (1.3 cm to 6.6 cm). For use with cattle, delivery system 10 has a diameter of about 0.5 inches to 1.5 inches (1.3 cm to 3.8 cm), and a length of about 1 inch to 4 inches (2.5 cm to 10 cm).

Delivery system 10, of the above described Figures, operates to deliver a beneficial agent 18 to a ruminant fluidic environment of use by a combination of thermodynamic and kinetic integrally performed activities. That is, in operation, thermo-responsive heat sensitive composition 17, in response to the temperature of the rumen, absorbs thermal energy, melts and forms a flowable, or a ribbon-like, semi-paste deliverable composition for delivering beneficial agent 18 through exit inducing passageway 27 in an exit member 25. As composition 17 melts, concomitantly therewith external fluid is imbibed through semipermeable wall 12 by displacement member 20, comprising an expandable hydrogel, or by an osmagent composition. The fluid imbibed into the hydrogel causes it to continuously expand and swell, or the imbibed fluid causes the osmagent composition to continuously form a solution, which expansion or solution, in either operation pushes and displaces thermo-responsive composition 17 from delivery system 10. The displacement member 20, in a preferred embodiment, operates while maintaining an intact immiscible boundary, as seen in FIG. 2 at interface 21, defined by heat-sensitive composition 17 and displacement member 20. Dense member 22 in delivery system 10 functions to keep the delivery system in the rumen thereby enabling delivery system 10 to deliver beneficial agent 18 at a controlled rate over a prolonged period of time, usually 1 day to about 180 days, or longer.

While FIGS. 1 through 11 illustrate various delivery systems 10 that can be made according to the invention, it is to be understood these delivery systems are not to be construed as limiting the invention, as the delivery system designed as a dispenser can take other shapes, sizes and forms for delivering beneficial agents to a biological environment of use. The delivery system can be used in hospitals, veterinary clinics, homes, farms, zoos, outpatient clinics, laboratories, on the range, in feed lots, for administering a drug to a warm-blooded animal including humans, and in other environments of use.

DETAILED DISCLOSURE OF THE INVENTION

In accordance with the practice of this invention, it has now been found wall 12 of delivery system 10 comprises in at least a part a semipermeable polymeric composition comprising semipermeable homopolymer compositions, semipermeable copolymer compositions, a composition comprising blends of polymers, and the like. Representative polymeric materials comprise cellulose monoesters, cellulose di esters, cellulose triesters, cellulose ethers, cellulose ester-ethers, mixtures thereof, and the like. The cellulosic polymers have a degree of substitution, on their anhydroglucose unit from greater than 0 up to 3 inclusive. The expression degree of substitution means the average number of hydroxyl groups originally present on the anhydroglucose unit that are replaced by a substituting group, or converted into another group. The anhydroglucose unit can be partially or completely substituted with groups such as acyl, alkanoyl, aroyl, alkyl, alkenyl, alkoxyl, halogen, carboalkyl, alkylcarbamate, alkylcarbonate, alkylsulfonate, alkylsulfamate, and like semipermeable polymer forming groups.

The semipermeable polymers typically comprise a member selected from the group consisting of cellulose acylate, cellulose diacylate, cellulose triacylate, cellulose acetate, cellulose diacetate, cellulose triacetate, mono-, di-, and tri-alkenylates, mono-, di- and tri-aroylates, and the like. Exemplary polymers include cellulose acetate having a D.S. of 1.8 to 2.3 and an acetyl content of 32 to 39.9%; cellulose diacetate having a D.S. of 1 to 2 and an acetyl content of 21 to 35%; cellulose triacetate having a 0.5. of 2 to 3 and an acetyl content of 34 to 44.8%; and the like. More specific cellulosic polymers comprise cellulose propionate comprising a D.S. of 1.8 and a propionyl content of 38.5%; cellulose acetate propionate having an acetyl content of 2.5 to 3%, an average propionyl content of 39.2 to 45% and a hydroxyl content of 2.8 to 5.4%; cellulose acetate butyrate having a D.S. of 1.8, an acetyl content of 13 to 15%, and a butyryl content of 34 to 39%; cellulose acetate butyrate having an acetyl content of 2 to 29.5%, a butyryl content of 17 to 53%, and a hydroxyl content of 0.5 to 4.7%; cellulose triacylates having a D.S. of 2.9 to 3 such as cellulose trivalerate, cellulose trilaurate, cellulose tripalmitate, cellulose trioctanoate, and cellulose tripropionate; cellulose diesters having a D.S. of 2.2 to 2.6 such as cellulose disuccinate, cellulose dipalmitate, cellulose dioctanoate, cellulose dicarpylate; cellulose propionate morphinobutyrate; cellulose acetate butyrate; cellulose acetate phthalate; and the like; mixed cellulose esters such as cellulose acetate valerate; cellulose acetate succinate, cellulose propionate succinate, cellulose acetate octanoate, cellulose valerate palmitate, cellulose acetate heptonate, and the like. Semipermeable polymers are known in U.S. Pat. No. 4,077,407, and they can be synthesized by procedures described in *Encyclopedia of Polymer Science and Technology*, Vol. 3, pp 325-354, 1964, published by Interscience Publishers, Inc., New York.

Additional semipermeable polymers comprise cellulose acetalaldehyde dehyde dimethyl cellulose acetate; cellulose acetate carbamate; cellulose acetate methylcarbamate; cellulose dimethylaminoacetate; a cellulose composition comprising cellulose acetate and hydroxypropylmethylcellulose; a composition comprising cellulose acetate and cellulose acetate butyrate; a cellulose composition comprising cellulose acetate butyrate and hydroxypropyl methyl cellulose; semipermeable polyamides; semipermeable polyurethanes; semipermeable polysulfones; semipermeable sulfonated polystyrenes; cross-linked, selectively semipermeable polymers formed by th coprecipitation of a polyaninon and a polycation as disclosed in U.S. Pat. Nos. 3,173,876; 3,276,586; 3,541,005; 3,541,006; and 3,546,142; selectively semipermeable polymers as disclosed by Loeb and Sourirajan in U.S. Pat. No. 3,133,132; semipermeable polystyrene derivatives; semipermeable poly(sodium styrenesulfonate); semipermeable poly(vinylbenzyltrimethyl) ammonium chloride; semipermeable polymers exhibiting a fluid permeability of $10^{-1}$ to $10^{-7}$ (cc . mil/cm$^2$ hr . atm) expressed as per atmosphere of hydrostatic or osmotic pressure difference across a semipermeable wall. The polymers are known to the art in U.S. Pat. Nos. 3,845,770; 3,916,899 and 4,160,020, and in *Handbook Of Common Polymers*, by Scott, J. R. and Roff, W. J., 1971, published by CRC Press, Cleveland, Ohio.

Wall 12 also can comprise a flux regulating agent. A flux regulatory agent is added to wall 12 compositions to assist regulating the fluid permeability of fluid through the wall. The flux regulating agent can be preselected to increase or decrease the liquid flux. Agents that produce a marked increase in permeability to fluid such as water or biological fluids are often essentially hydrophilic, while those that produce a marked decrease to fluids such as water or biological fluids are essentially hydrophobic. The amount of regulator in the wall, when incorporated therein, generally is from about 0.01% to 30% by weight or more. The flux regulator agents in one embodiment that increase flux include polyhydric alcohols, polyalkylene glycols, polyalkylenediols, polyesters of alkylene glycols, and the like. Typical flux enhancers include polyethylene glycol 300, 400, 600, 1500, 4000, 6000 and the like; low molecular weight glycols such as polypropylene glycol, polybutylene glycol and polyamylene glycol; the polyalkylenediols such as poly(1,3-propanediol), poly(1,4-butanediol), poly(1,6-hexanediol), and the like; aliphatic diols such as 1,3-butylene glycol, 1,4-pentamethylene glycol, 1,4-hexamethylene glycol, and the like; alkylene triols such as glycerine, 1,2,3-butanetriol, 1,2,4-hexanetriol, 1,3,6-hexanetriol and the like; ester such as ethylene glycol diproprionate, ethylene glycol butyrate, butylene glycol diproprionate glycerol acetate esters, and the like. Representative flux decreasing agents include phthalates substituted with an alkyl, an alkoxy or with both an alkyl and alkoxy group such as diethyl phthalate, dimethoxyethyl phthalate, dimethyl phthalate, and di(2-ethylhexyl) phthalate; aryl phthalates such as triphenyl phthalate, and butyl benzyl phthalate; insoluble salts such as calcium sulphate, barium sulphate, calcium phosphate, and the like; insoluble oxides such as titanium oxide; polymers in powder, granule and like form such as polystyrene, polymethylmethacrylate, polycarbonate, and polysulfone; esters such as citric acid esters esterified with long chain alkyl groups; inert and substantially water impermeable fillers; resins compatible with cellulose based wall forming materials; and the like.

Other materials that can be used to provide wall 12 for imparting flexibility and elongation properties to the wall, for making the wall less to nonbrittle and to render tear strength include phthalate plasticizers such as dibenzyl phthalate, dihexyl phthalate, butyl octyl phthalate, straight, chain phthalates of six to eleven carbons, diisononyl phthalate, diisodecyl phthalate, and the like. The plasticizers include nonphthalates such as triacetin, triisononyl timellitate, sucrose acetate isobutyrate, epoxidized soybean oil, tributyl citrate, triethyl citrate and the like. The amount of plasticizer in a wall when incorporated therein is about 0.01% to 20% by weight, or higher.

Expandable member 20 has a shape that corresponds to the internal shape of wall 12 and compartment 16 is made from a hydrogel. composition, or from an osmagent composition. The hydrogel composition is non-cross-linked or optionally cross-linked and it possesses osmotic properties, such as the ability to imbibe an exterior fluid through semipermeable wall 12, and exhibit an osmotic pressure gradient across semipermeable wall 12 against a fluid outside delivery system 10. The materials used for forming the swellable, expandable member, are polymeric materials neat, and polymeric materials blended with osmotic agents that interact with water or a biological fluid, absorb the fluid and swell or expand to an equilibrium state. The polymer exhibits the ability to retain a significant fraction of imbibed fluid in the polymer molecular structure. The polymers in a preferred embodiment are gel polymers that can swell or expand to a very high degree, usually exhibiting a 2 to 50 fold volume increase. The swellable, hydrophilic polymers, also known as osmopolymers can be non-cross-linked or lightly cross-linked. The cross-links can be covalent or ionic bonds with the polymer possessing the ability to swell in the presence of fluid, and when cross-linked it will not dissolve in the fluid. The polymer can be of plant, animal or synthetic origin. Polymeric materials useful for the present purpose comprises poly(hydroxyalkyl methacrylate) having a molecular weight of from 5,000 to 5,000,000; poly(vinylpyrrolidone) having a molecular weight of from 10,000 to 360,000; anionic and cationic hydrogels; poly(electrolyte) complexes; poly(vinyl alcohol) having a low acetate residual; a swellable mixture of agar and carboxymethyl cellulose; a swellable composition comprising methyl cellulose mixed with a sparingly cross-linked agar; a water-swellable copolymer produced by a dispersion of finely divided copolymer of maleic anhydride with styrene, ethylene, propylene, or isobutylene; water swellable polymer of N-vinyl lactams; and the like.

Other gelable, fluid imbibing and retaining hydrogel, hydrophilic polymers useful for forming the hydrophilic, expandable push member 20 include pectin having a molecular weight ranging from 30,000 to 300,000; polysaccharides such as agar, acacia, karaya, tragacanth, algins and guar; Carbopol ® acidic carboxy polymer and its salt derivatives; polyacrylamides; water-swellable indene maleic anhydride polymers; Goodrite ® polyacrylic acid having a molecular weight of 80,000 to 200,000; Polyox ® polyethylene oxide polymers having a molecular weight of 100,000 to 5,000,000; starch graft copolymers; AquaKeep ® acrylate polymers with water absorbability of about 400 times its original weight; diesters of polyglucan; a mixture of cross-linked polyvinyl alcohol and poly(N-vinyl-2-pyrrolidone); zein available as prolamine; poly(ethylene glycol) having a molecular weight of 4,000 to 100,000; and the like. In a preferred embodiment, the expandable member 20 is formed from polymers and polymeric compositions that are thermoformable. Representative polymers possessing hydrophilic properties are known in U.S. Pat. Nos. 3,865,108; 4,002,173; 4,207,893; 4,327,725, and in *Handbook of Common Polymers:* by Scott and Roff, published by Cleveland Rubber Company, Cleveland, Ohio.

The swellable, expandable polymer 20, in addition to providing a driving source for delivering a beneficial agent 18 from the dispenser 10, further serves to function as a supporting matrix for an osmotically effective solute. The osmotic solute can be homogeneously or heterogeneously blended with the polymer to yield the desired expandable member 20. The composition in a presently preferred embodiment comprises at least one polymer and at least one osmotic solute. Generally, a composition will comprise about 20% to 95% by weight of polymer and 80% to 5% by weight of osmotic solute, with a presently preferred composition comprising 35% to 75% by weight of polymer and 65% to 25% by weight of osmotic solute with the total weight of the composition equal to 100% by weight.

The osmotically effective compound that can be used neat or blended homogeneously or heterogeneously with the swellable polymer 20, to form a push member, are the osmotically effective solutes that are soluble in the fluid imbibed into the swellable polymer, and exhibit an osmotic pressure gradient across the semipermeable wall against an exterior fluid. Osmotically effective compounds are known also as osmagents. Expandable member 20, in another embodiment, comprises an osmagent as the driving member for displacing the thermo-responsive composition from delivery system 10. In this embodiment, a compressed tablet comprising an osmagent is shaped for placement in lumen 16 for displacing the thermo-responsive composition from delivery system 10. Representative of osmotically effective osmagents that can be blended with the hydrogel, or used to provide an osmotic driving tablet comprise magnesium sulfate, magnesium chloride, sodium chloride, lithium chloride, potassium sulfate, sodium sulfate, mannitol, urea, sorbitol, inositol, sucrose, potassium chloride, glucose, and the like. The osmotic pressure in atmospheres, ATM, of the osmagents suitable for the invention will be greater than zero ATM, generally from eight ATM up to 500 ATM, or higher.

The thermo-responsive composition 17, comprising agent 18 homogeneously or heterogeneously dispersed or dissolved therein, in a presently preferred embodiment is a heat sensitive, hydrophilic or hydrophobic composition that exhibits solid-like properties at room temperature of 21° C. to 25° C., and within a few centigrade degrees thereof, and exhibits in a preferred embodiment a melting point that approximates mammalian body temperatures, and within a few centigrade degrees thereof. The present invention uses the phrases "melting point", "softening point", "pour point", or "liquifies" to indicate the temperature at which the thermo-responsive composition melts, undergoes dissolution, or forms a paste-like ribbon, dissolves to form a dispensable carrier so it can be used for dispensing agent 18 from delivery system 10.

The term thermo-responsive composition 17 as used for the purpose of this invention includes thermoplastic compositions capable of softening, or becoming dispensable in response to heat and hardening again when cooled. The term also includes thermotropic compositions capable of undergoing change in response to the application of energy in a gradient manner. These thermo-responsive compositions 17 are temperature sensitive in their response to the application or withdrawal of energy. The term "thermo-responsive" as used for the purpose of this invention in a preferred embodiment denotes the physical-chemical composition to exhibit solid, or solid-like properties at temperatures of 21° C. to 25° C. and usually up to 31° C., and become fluid, semisolid, or viscous when disturbed by heat at temperatures from 31° C., usually in the range of 31° C. to 45° C. and more preferably at mammalian body temperatures of 37° C. to 42° C. Thermo-responsive carrier 17 is heat-sensitive and preferably anhydrous and it possesses the properties for melting, dissolving, undergoing dissolution, softening, or liquefying at the elevated temperatures, thereby making it possible for the dispenser 10 to deliver the thermo-responsive carrier with the beneficial agent 18 homogeneously or heterogeneously blended therein. The thermo-responsive carrier can be lipophilic, hydrophilic or hydrophobic. Another important property of the carrier is its ability to maintain the stability of the agent contained therein during storage and during delivery of the agent. Representative thermo-responsive compositions and their melting points are as follows: cocoa butter 32°-34° C.; cocoa butter plus 2% beeswax 35°-37° C.; propylene glycol monostearate and distearate 32°-35° C.; hydrogenated oils such as hydrogenated vegetable oil 36°-37.5° C.; 80% hydrogenated vegetable oil and 20% sorbitan monopalmitate 39-39.5%; 80% hydrogenated vegetable oil and 20% polysorbate 60, 36°-37° C.; 77.5% hydrogenated vegetable oil, 20% sorbitan trioleate and 2.5% beeswax 35°-36° C.; 72.5% hydrogenated vegetable oil, 20% sorbitan trioleate, 2.5% beeswax and 5.0% distilled water, 37°-38° C.; mono-, di-, and triglycerides of acids having from 8-22 carbon atoms including saturated and unsaturated acids such as palmitic, stearic, oleic, linoleic, linolenic and arachidonic; glycerides of fatty acids having a melting point of at least 32° C. such as monoglycerides, diglycerides and triglycerides of vegetable fatty acids having 10 to 18 carbon atoms obtained from coconut oil, olive oil and the like; partially hydrogenated cottonseed oil 35°-39° C.; hardened fatty alcohols and fats 33°-36° C.; hexadienol and hydrous lanolin triethanolamine glyceryl monostearate 38° C.; eutectic mixtures of mono-, di-, and triglycerides 35°-39° C.;

Witepsol® #15, triglyceride of saturated vegetable fatty acid with monoglycerides 33.5°–35.5° C.; Witepsol® H32 free of hydroxyl groups 31°–33° C.; Witepsol® W25 having a saponification value of 225–240 and a melting point of 33.5°–35.5° C.; Witepsol™ E75 having a saponification value of 220–230 and a melting point of 37°–39° C.; a polyalkylene glycol such as polyethylene glycol 1000, a linear polymer of ethylene oxide, 38°–41° C.; polyethylene glycol 1500, melting at 38°–41° C.; polyethylene glycol monostearate 39°–42.5° C.; 33% polyethylene glycol 1500, 47% polyethylene glycol 6000 and 20% distilled water 39°–41° C.; 30% polyethylene glycol 1500, 40% polyethylene glycol 4000 and 30% polyethylene glycol 400, 33°–38° C.; mixture of mono-, di-, and triglycerides of saturated fatty acids having 11 to 17 carbon atoms, 33°–35° C.; block polymer of 1,2-butylene oxide and ethylene oxide; block polymer of propylene oxide and ethylene oxide; block polymer of polyoxyalkylene and propylene glycol; microcrystalline waxes that become semisolid at 37° C., and the like. The thermo-responsive composition is a means for storing a beneficial agent in a solid composition at a temperature of 20°–32° C., maintaining an immiscible boundary at the swelling composition interface, and for dispensing the agent in a flowable composition at a temperature greater than 32° C., and preferably in the range of 32°–40° C. The thermo-responsive composition on being dispensed into a biological environment are easily excreted, metabolized, assimilated, or the like, for effective use of the beneficial agent.

The term "beneficial agent 18" as used herein includes medicines or drugs, nutrients, vitamins, food supplements and other agents that benefit an animal, including a warm-blooded animal, and humans, and more particularly a ruminant animal. The beneficial agent can be insoluble to very soluble in the temperature sensitive material housed in the delivery system 10. The amount of agent present in a delivery system 10 can be from 10 ng to 40 g or more. The delivery system can house various amounts of the beneficial agent, for example, 75 ng, 1 mg, 5 mg, 100 mg, 250 mg, 750 mg, 1.5 mg, 2 g, 5 g, 10 g, 15 g, and the like. A single delivery system can be administered to a ruminant, or more than one delivery system can be administered to a ruminant during a therapeutic program.

Representative of beneficial medicaments 18 that can be dispensed using the delivery system of this invention include anthelmintics such as mebendazole, levamisole, albendazole, cambendazole, fenbendazole, parbendazole, oxfendazole, oxybendazole, thiabendazole, trichlorfon, praziquantel, morantel and pirantel, and the like; antiparasitic agents such as avermectins and ivermectin, as disclosed in U.S. Pat. Nos. 4,199,569 and 4,389,397 both assigned to Merck & Co., and in *Science* Vol. 221, pages 823 to 828, 1983, wherein said invermectin antiparasitic drug are disclosed as useful for aiding in controlling commonly occurring infestations in animals, such as roundworms, lung worms and the like, and said invermectin also being useful for the management of insect infestations such as grub, lice, mange mite, and the like; antimicrobial agents such as chlortetracycline, oxytetracycline, tetracycline, streptomycin, dihydrostreptomycin, bacitracins, erythromycin, ampicillins, penicillins, cephalosporins, and the like; sulfa drugs such as sulfamethazine, sulfathiazole, and the like; growth-stimulants such as Monesin ® sodium and Elfazepa ®; defleaing agents such as dexamethasone and flumethasone; rumen fermentation manipulators and ionophores such as lasalocid, virginamycin and ronnel; minerals and mineral salts; anti-bloat agents such as organopoly siloxanes; hormone growth supplements such as stilbestrol; vitamins; antienteritis agents such as furazolidone; nutritional supplements such as lysine monohydrochloride, methionine, magnesium carbonate; sodium selenite, cobalt, and the like.

Representative of compound 19 used by the present invention to increase the viscosity and/or the yield stress of the thermo-responsive composition comprises compounds containing silicon, such as fumed silica, reagent grade sand, precipitated silica, amorphous silica, colloidal silicon dioxide, fused silica, silica gel, quartz, particulate siliceous materials commercially available as Syloid ®, Cabosil ®, Aerosil ®, Whitelite ®, and the like. Other inert compounds include precipitated calcium carbonate, aluminum carbonate, manganese fluosilicate, manganese pyroselenite, nickel sulfite, potassium silicate, and the like. The viscosity or stress inducing agent in a presently preferred embodiment is soluble, or miscible or dispensable in the heat sensitive formulation and it can be homogeneously or heterogeneously blended or dispersed therein. The term "viscosity" as used herein denotes the property of a fluid, semifluid, or viscous state that enables it to develop and maintain an amount of shearing stress dependent upon the velocity of flow and then to offer continued resistance to flow. The expression "yield stress" as used herein generically denotes an increased internal stress of the heat sensitive formulation to the point that strain yields, that is the point where the heat sensitive formulation begins to flow. The amount of inert, non-toxic, pharmaceutically acceptable compound used for the present purpose usually is about 0.01% by weight to about 35% by weight.

The dense member 22, also referred to as densifier 22, used in delivery system 10 is dense enough to retain system 10 in the rumen-reticular sac of a ruminant. Dense member 22 lets system 10 remain in the rumen over a prolonged period of time rather than letting it pass into the alimentary tract and be eliminated therefrom. As delivery system 10 remains in the rumen, beneficial active agent 18 is delivered by delivery system 10 at a controlled rate to the ruminant over time. Generally, dense member 20 will have a density of from about 0.8 to 8, or higher, with the density in a presently preferred embodiment exhibiting a specific gravity of from 1.2 to 7.6. For the ruminants cattle and sheep, it is presently preferred dense member 22 exhibit a density such that there is a resulting system density of about 3. Materials that have a density that can be used for forming dense member 22 include iron, iron shot, iron shot coated with iron oxide, iron shot magnesium alloy, steel, stainless steel, copper oxide, a mixture of cobalt oxide and iron powder, and the like. Dense member 22 in delivery system 10 can embrace different embodiments. For example, dense member 22 as seen in FIG. 2 is machined or cast as a single, solid piece made of stainless steel having a density of 7.6. The solid member 22 is made having a curved shape that corresponds to the internal shape of delivery system 10. The solid member as seen in FIG. 2 has an axially aligned bore that extends through the length of the unit member that serves as a passageway for letting thermo-responsive composition 17 comprising beneficial agent 18 leave lumen 16 and be dispensed through exit member 25 to the rumen. In another embodiment, dense member 22 is manufactured as a solid body as seen in FIG. 4. Density member 22, as seen in FIG. 6, can be dispersed throughout an expandable member 20. In this latter manufacture, a density increasing member is homogeneously or heterogeneously dispersed throughout the expandable hydrogel for initially retaining delivery system 10 in the rumen-reticular sac of a ruminant. Material that have a density of from 1 to 8 that can be blended with the hydrogel expandable member include iron particles, iron shot, iron shot coated with iron oxide, a mixture of iron and copper oxide powder, and the like. The weight can be blended with the hydrogel during polymerization, by blending solvent casting and evaporating, by compressing a blend, and the like. The amount of weight means blended with a hydrogel is about 0.5 to 70 weight percent, or an amount sufficient to produce the desired density. Density, specific gravity and specific volume determination are easily performed by procedures known in the art as disclosed in Remington's Pharmaceutical Sciences, Vol. 14, pp 95-100, edited by Osol, 1970, by Mack Publishing Co., Easton, Penna.

Layer 28, as seen in FIG. 9, is positioned between the active formulation 17 and the expandable driving member 20. Layer 28 substantially maintains the separate identity of the thermo-responsive composition containing the beneficial agent and the expandable member, and in a presently preferred embodiment layer 28 is a wax. The term wax as used herein generically denotes a petroleum based food-grade wax or an ester of a high molecular weight alcohol. Materials useful for this purpose include waxes, which are a different wax composition than a wax comprising the thermo-responsive composition; for example, the former can be a higher melting point wax. The waxes acceptable for this present purpose exhibit a melting point or a solidification point of about 45° C. to 110° C. and they are selected from the group consisting of mineral, vegetable, plant, animal, petroleum, and synthetic waxes. Representative waxes include a member selected from the group including the following wax and its melting range: montan wax, 80°-90° C., ozokerite wax, 55°-110° C., usually 70° C.; carnauba wax, 84°-86° C.; myricyl cerotate wax, 85° C.; beeswax, 63° C.; spermaceti, 45° C.; ceresin wax, 48° C.; gama wax, 47° C.; Japan wax, 63° C.; ouricury wax, 83° C.; ceresin wax, 68°-72°C.; castor wax, 85°C.; Witco wax, 72° C.; microcrystalline petroleum wax, 66°-88° C. and the like. Additionally, reinforcing agents such as Cab-o-sil can be incorporated into the wax for improving structural integrity.

Layer 28 optionally comprises a film-forming polymer that is capable of receiving and transmitting an applied force, such as olefin polymers, vinyl polymers, synthetic condensation polymers, natural polymers, and organosilicon polymers. Representative of specific polymers include polyethylene, polypropylene, polytetrafluoroethylene, polystyrene, polyvinyl acetate, polyvinyl formal, cross-linked polyvinyl acetate, polyvinyl butyral polyacrylate, polymethyacrylate, polyvinylchloride, cellulose acetate, polyamides, polyester, rubber, styrene butadiene rubber, polyurethane, polysilicone, and the like. The lamina can have a thickness from 1 mil (0.0254 mm) to 590 mil (15 mm), or more, for effectively transmitting the in vivo generated force.

Wall 12 of delivery system 10 can be made by conventional thermoforming polymeric processes, such as spraying a mandrel, dipping a mold into a wall forming composition, blow molding, vacuum forming, compression molding, injection molding, extrusion and the like.

Exemplary solvents suitable for manufacturing the walls include inert inorganic and organic solvents that do not adversely harm the materials, the wall, the beneficial agent, and other components comprising the final dispenser. The solvents broadly include a member selected from the group consisting of aqueous, alcohol, ketone, ester, ether, aliphatic hydrocarbon, halogenated, cycloaliphatic, aromatic, and heterocyclic solvents, and mixtures thereof. Solvents for the present purpose are disclosed in U.S. Pat. Nos. 4,729,793 and 4,772,474 by Eckenhoff, Cortese and Landrau.

DISCLOSURE OF EXAMPLES OF THE INVENTION

EXAMPLE 1

A delivery system manufactured in the shape of a dispenser adapted for the controlled delivery of ivermectin to an animal is made as follows: first, a membrane cup in the shape of a dispenser is injection molded from a wall-forming composition comprising 50.5% cellulose acetate butyrate 171-15 having a 17.1% butyryl content, a 29.5% acetyl content and a 1.5% hydroxyl content; 17.5% cellulose acetate 398-10 having a 39.8% acetyl content; 22% Citroflex ® 4 tributyl citrate, 6% Citroflex ® 2 triethyl citrate and 4% polyethylene glycol 400. The final injection molded cup weighed about 10 grams each.

Next, an expandable driving member designed as an osmotic tablet is manufactured in a shape that corresponds to the internal shape of the injection molded cup. The expandable driving member composition comprises 2.5 g of sodium chloride, 5.8 g of the sodium salt of polyacrylic acid polymer available as Carbopol ® 934P, 0.07 g of Povidone ® polyvinyl pyrrolidone, and 0.10 g of magnesium stearate. The composition was compressed under 10 tons into an osmotic tablet, 0.850 inches in diameter, 0.66 inches in height, and having a tablet density approximately 1.56 g/cc.

Next, 600 g of ivermectin was added with high shear mixing at 90° C. to 3400 g of pharmaceutically acceptable wax exhibiting a melting point of 150°/160° F., a Saybolt viscosity of 75/90 at 210° F., and a light yellow color. The two ingredients were blended at 90° C. for about 30 minutes. The high shear mixing was turned off and the anchor blade and impeller blade activated at 35% speed to ensure a homogenous blend. Then, a vacuum, 10 inches of Hg, was pulled for 30 minutes and the mixture cooled to 74° C., after which the impeller blade was turned off and the vacuum released. The mixing tank then was pressurized to 5 psig. using nitrogen.

Next 500 g of microcrystalline wax exhibiting a melting point of 150°/160° F., a needle penetration at 77° F. of 35/45, and Saybolt viscosity of 75/90 at 210° F. was added to 500 g of microcrystalline wax exhibiting a melting point of 180°/190° F., a needle penetration of 15/20 at 77° F. and a Saybolt viscosity of 75/90 at 210° F. and the two ingredients were blended at 90° C. to form a homogenous blend. The blend is designed for use as a partition formulation and the blend was made using a high shear rotor stator blade. After 10 minutes of mixing, the rotor stator blade was turned off and a vacuum pulled on the resulting mixture for about 30 minutes.

The dispenser was assembled by first placing the osmotion expansion tablet into the membrane cup. The membrane cup was preheated at 60° C. for about 5 minutes. Next, 1.95 g of the partition formulation was added to the membrane cup in contacting relation with the osmotic expansion tablet. After cooling for 2 to 6 minutes, 9.5 g of the formulation comprising the ivermectin was added to the membrane cup, followed by cooling the cup to 60° C. for 8 minutes. Then, a density element comprising iron with a central bore and dimensioned to conform to the inside of the membrane cup was placed into the cup. The density element was preheated to 65° C., and inserted into the membrane cup until the bottom of the density element contacted the thermo-responsive ivermectin formulation.

Figure 12:
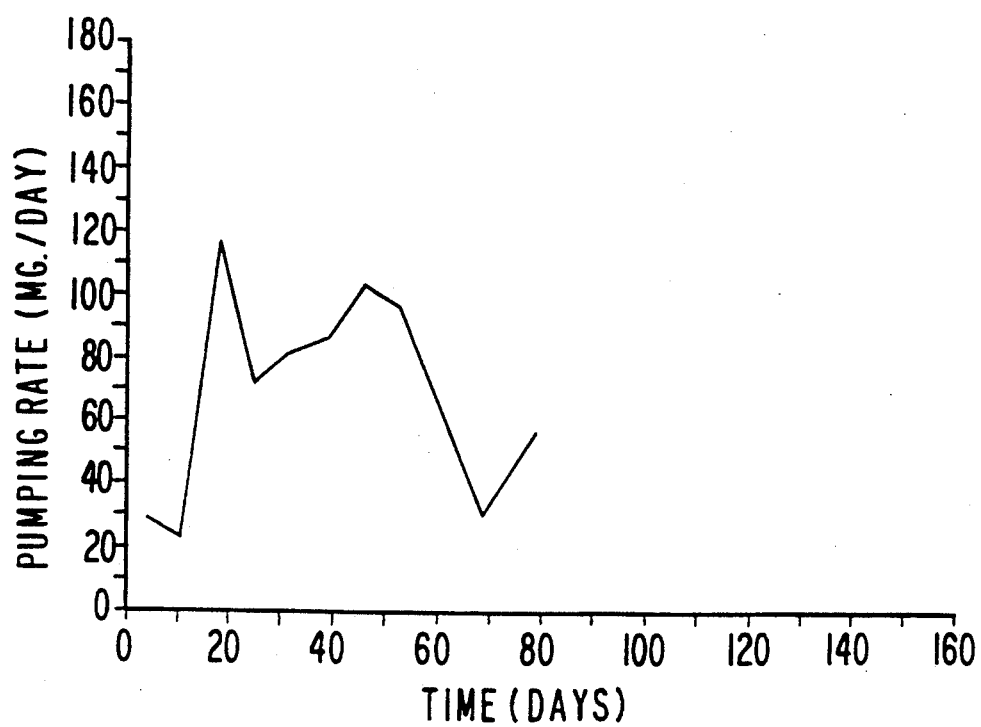
FIGS. 12 through 22 are graphs that depict the release rate pattern for delivery systems under various testing environments; and, FIG. 23 is a cross-sectioned view of a delivery system comprising a prehydration permeant.

Next, the membrane cup was rotated in front of a hot air gun until the tip of the membrane softened and became thermoplastic. The membrane cup next was placed into a crimping fixture pressurized with 90 psi, compressed air, followed by a crimping head activated, positioned and rotated on top of the membrane cup for 15 seconds to yield the dispenser. Accompanying FIG. 12 depicts the release rate patterns for ivermectin for a dispenser made by this example.

EXAMPLE 2

A delivery system manufactured in the shape of a dispenser adapted for administering a beneficial agent to an animal was made by following the procedure of Example 1. The delivery system was made as described, except as follows: 600 g of ivermectin was added with high shear mixing at 90° C. to 3320 g of microcrystalline food grade wax having a melting point of 150°–160° F. and a Saybolt viscosity at 210° F. of 75/90, and 80 g of silicon dioxide. The silicon dioxide increases the viscosity and yield stress of the ivermectin-containing formulation. The three ingredients were blended with a rotor stator blade at 90° C. for 30 minutes. Then, the high shear mixing was turned off and the anchor and impeller blades were activated at 35% speed followed by pulling 10 inches of Hg vacuum for 30 minutes. Then, the mixture was cooled to approximately 74° C., the impeller blade turned off and the vacuum released. Next, the mixing tank was pressurized to 5 psi using nitrogen gas.

Figure 13:
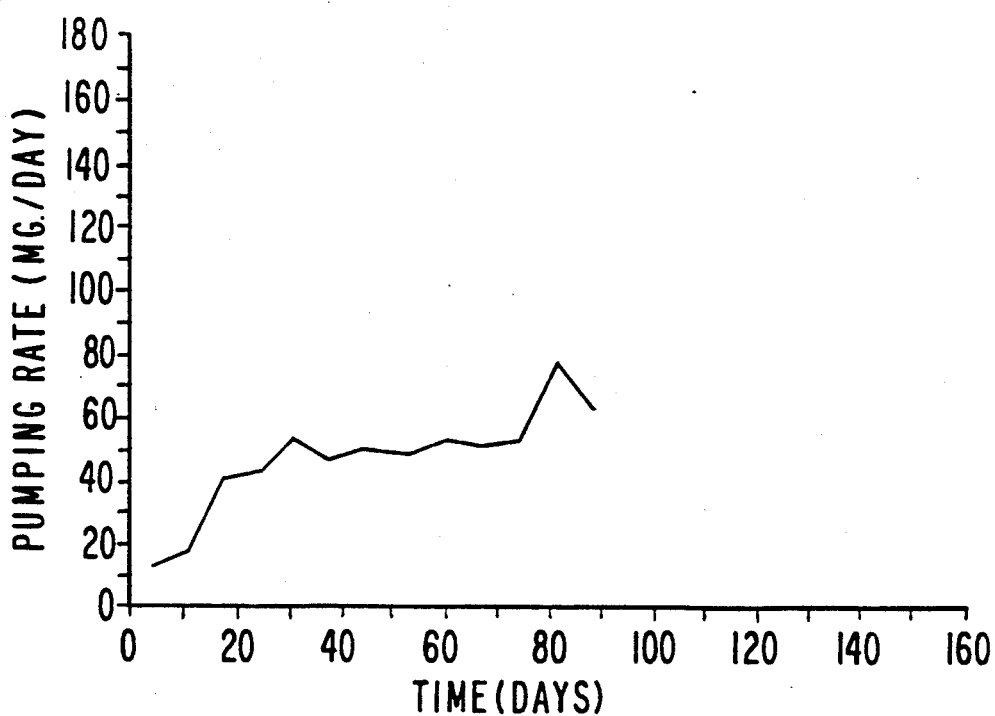

Next, 490 g of food grade microcrystalline wax, as described in the paragraph immediately above, was added to 490 g of a food grade microcrystalline wax having a 180°–190° F. melting point and a Saybolt viscosity at 210° F. of 75/90, and the mixture heated to 90° C. Then, 20 g of silicon dioxide was added to the molten waxes and the mixture blended using a high shear rotor stator blade for 10 minutes. After 10 minutes of mixing, the high shear rotor stator blade was turned off and 10 inches of Hg pulled on the mixture for 30 minutes. The dispenser was assembled as described in Example 1. Accompanying FIG. 13 illustrates the in vivo release rate profile for the dispenser made according to this example. The addition of the silicon dioxide improved the uniformity of the release rate profile over that of FIG. 12.

EXAMPLE 3

Figure 14:
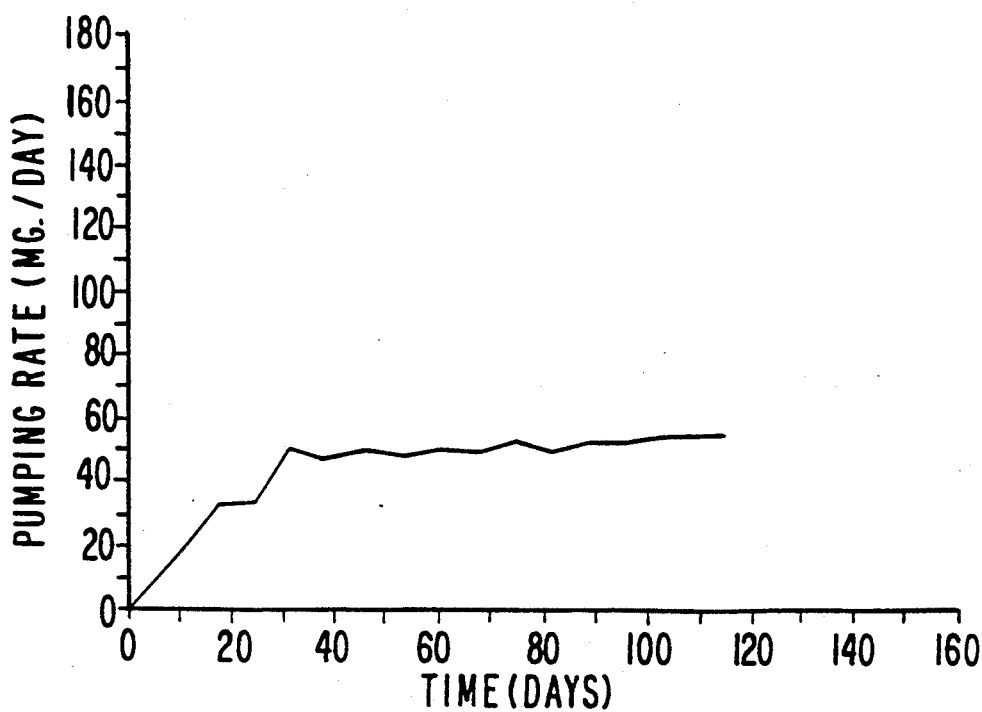

A delivery system manufactured in the shape of a dispenser for the controlled delivery of the beneficial agent ivermectin was made according to the procedures of Example 2. In this example, an exit member made as a stainless steel grid with a plurality of openings of approximately 18 mesh was placed in the exit bore of the density 15 element. The wall of the membrane cup was crimped as described above. Accompanying FIG. 14 depicts the release rate profile for the dispenser made according to this Example. The placement of the stainless steel grid has significantly improved the uniformity of the release rate profile over that of FIGS. 12 and 13.

Example 4

Figure 15:
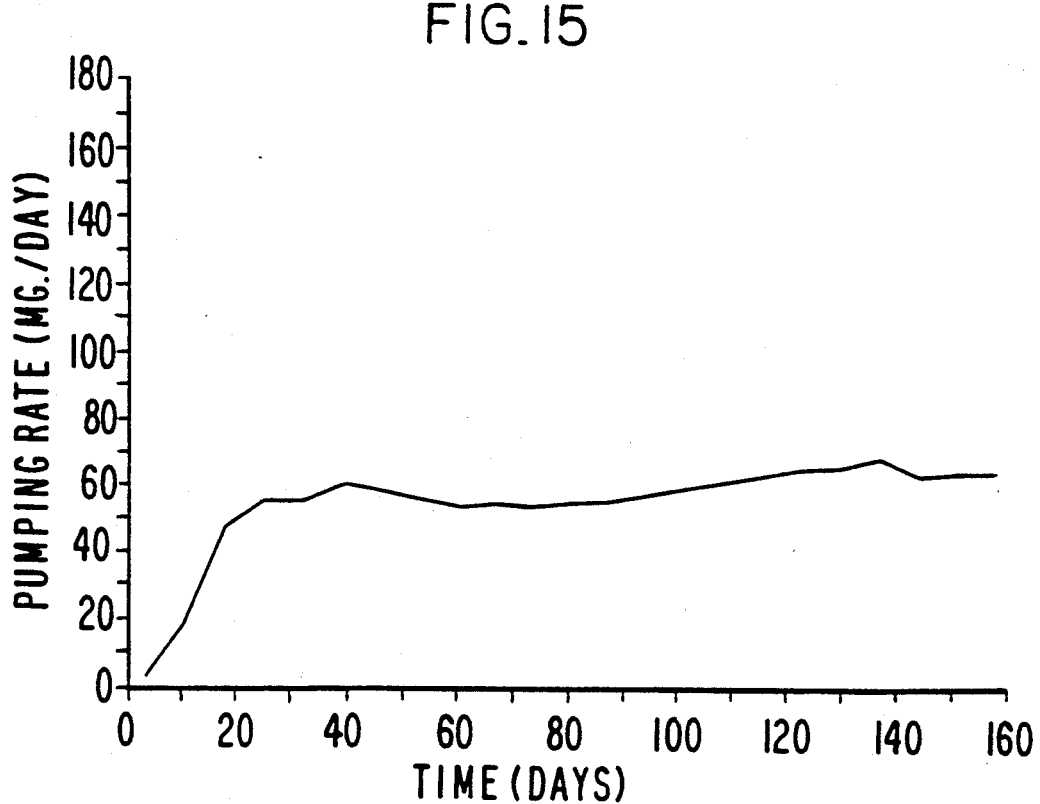

A delivery system for the controlled delivery of the beneficial agent ivermectin was made according to the procedure of Example 2, with all procedures as described except for the manufacturing steps described in this example. In this example 1% of titanium dioxide was dry blended into the composition comprising the membrane cup. The membrane cup was injection molded using the procedures set forth in Example 1. The stainless steel exit member of Example 3 was replaced with a polymeric exit member manufactured from nylon as seen in drawing FIGS. 3a, 3b, 3c, and 9. The uniform release rate profile from the dispenser made according to this example is illustrated in FIG. 15.

EXAMPLE 5

Figure 16:
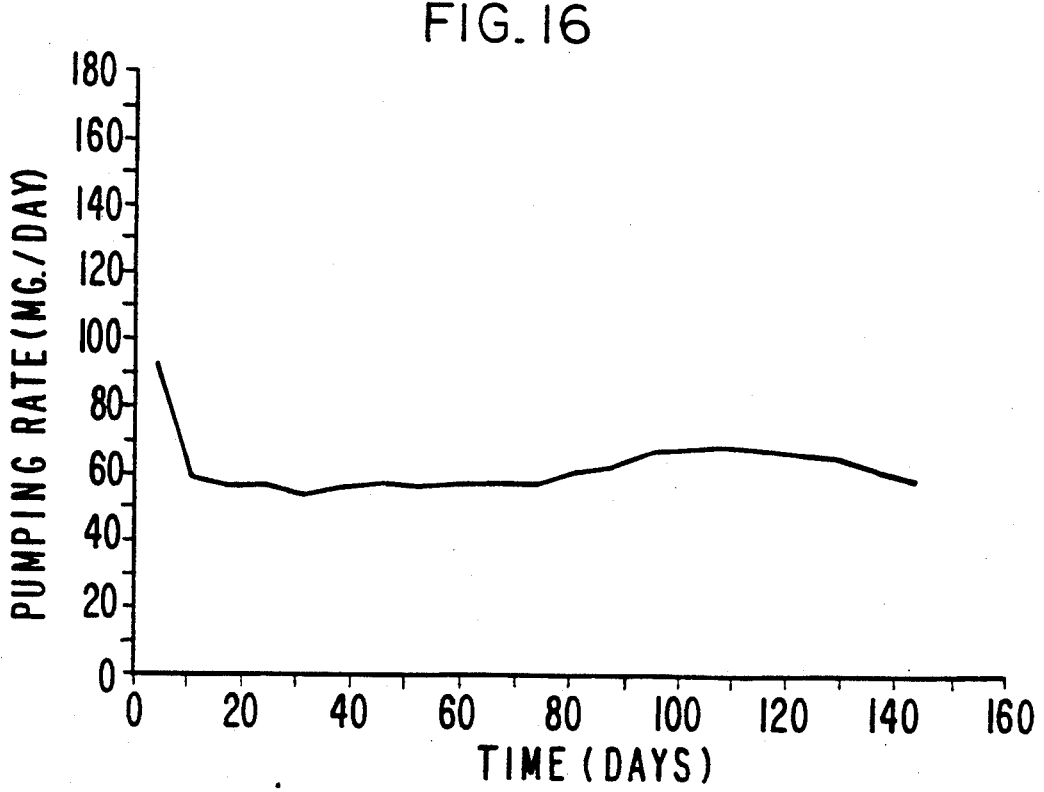
Figure 23:
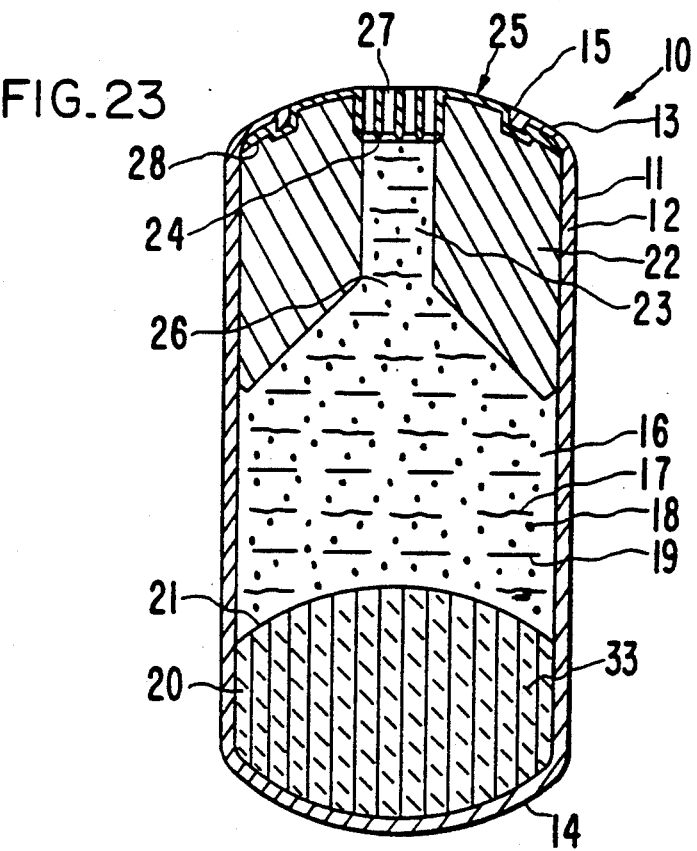

A delivery system for the controlled delivery of the beneficial drug ivermectin with instant start-up was made as set forth in Example 4, except as follows: the delivery system of Example 4 was prehydrated for 18 days at 40° C. in deionized water, after which the prehydration temperature was trampled down over 8 days at approximately 2°–3° C. per day. The delivery system was packaged and stored for at least one week prior to use. The delivery system can be prehydrated with a permeant by immersing, partial immersion, dipping, spraying, or the like in a permeant such as water, distilled water, a buffer, a physiologically acceptable fluid such as saline or the like. The delivery system can be prehydrated with a permeant for 1 hr. to 18 days or longer, at any temperature usually at 20° C. to 40° C. or the like. The prehydration is provided to reduce drug delivery start-up time, or to provide instant drug delivery, especially when delivered to an animal. Sometimes, dependent on the manufacture, the delivery system exhibits a 2 to 3 week start-up, while a prehydrated delivery system begins to deliver drug during the first week, usually starting in 24 hours. The volume of prehydration permeant introduced into a delivery system is usually about 0.025 g to 10 g of permeant, and more preferably from 0.1 g to 3 g of permeant. The amount of permeant imbided into a delivery system usually is greater than 1% by weight of the displacement means, and in a presently preferred amount of about 5% to 40% of the weight of the displacement means. FIG. 16 depicts the in vivo release rate for a delivery system made according to this procedure FIG. 23 depicts in cross-section a prehydrated delivery system provided by the invention, wherein 33 denotes a prehydration permeant 33 in displacement means 20.

EXAMPLES 6 to 11

Delivery systems were made according to the above described procedures. In the following examples, the delivery profile for delivery systems were measured in different test environments. The test environments were in vitro and in vivo. The in vitro test environments included water, artificial ruminal fluid sparged with a 50/50% mixture of nitrogen and carbon dioxide, artificial ruminal fluid sparged with 25/75% nitrogen/carbon dioxide, and an in vivo environment of a fistulated cow.

The release rate pattern for delivery systems is illustrated in the following drawing figures. Drawing FIG.

Figure 17:
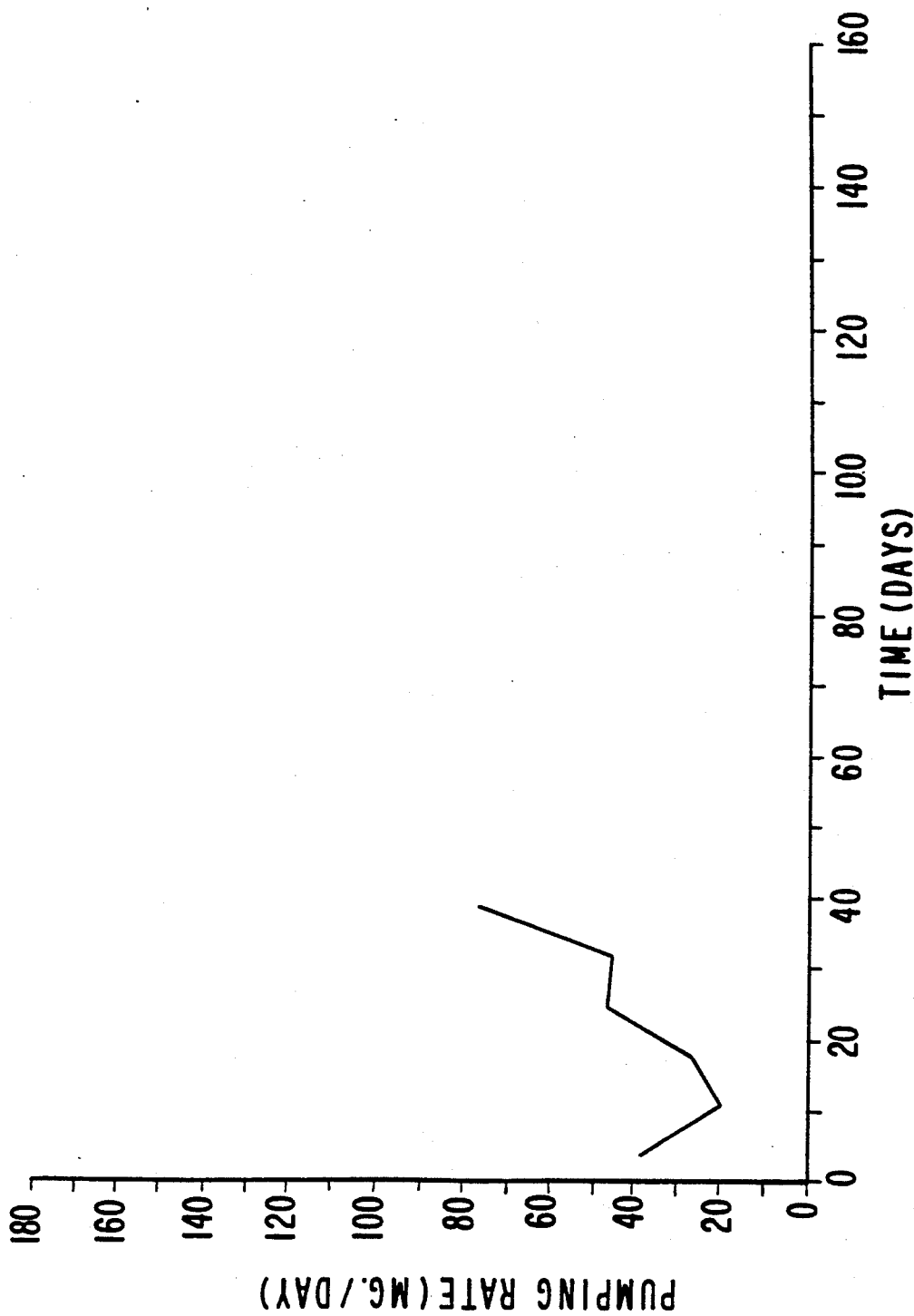
Figure 18:
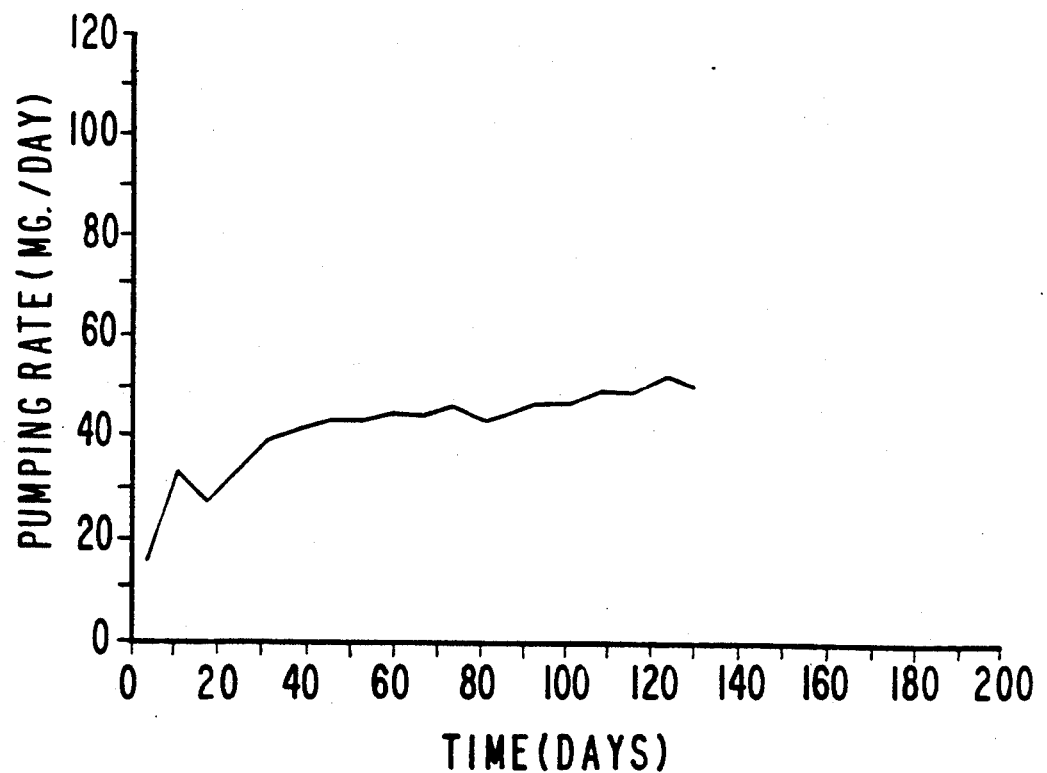
Figure 19:
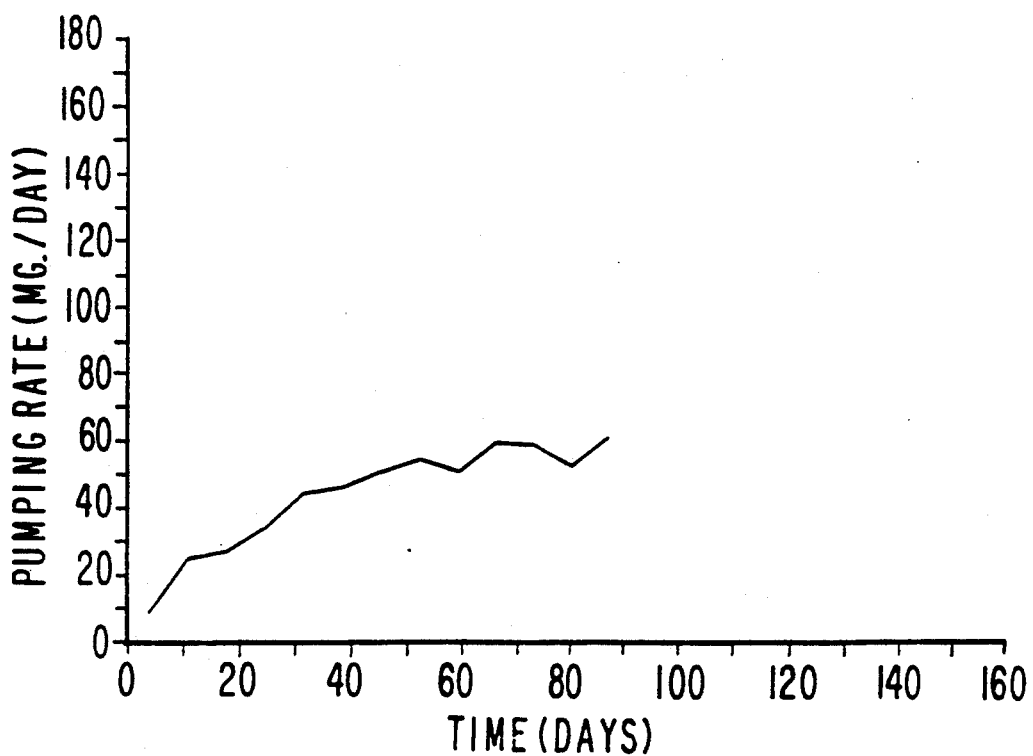
Figure 20:
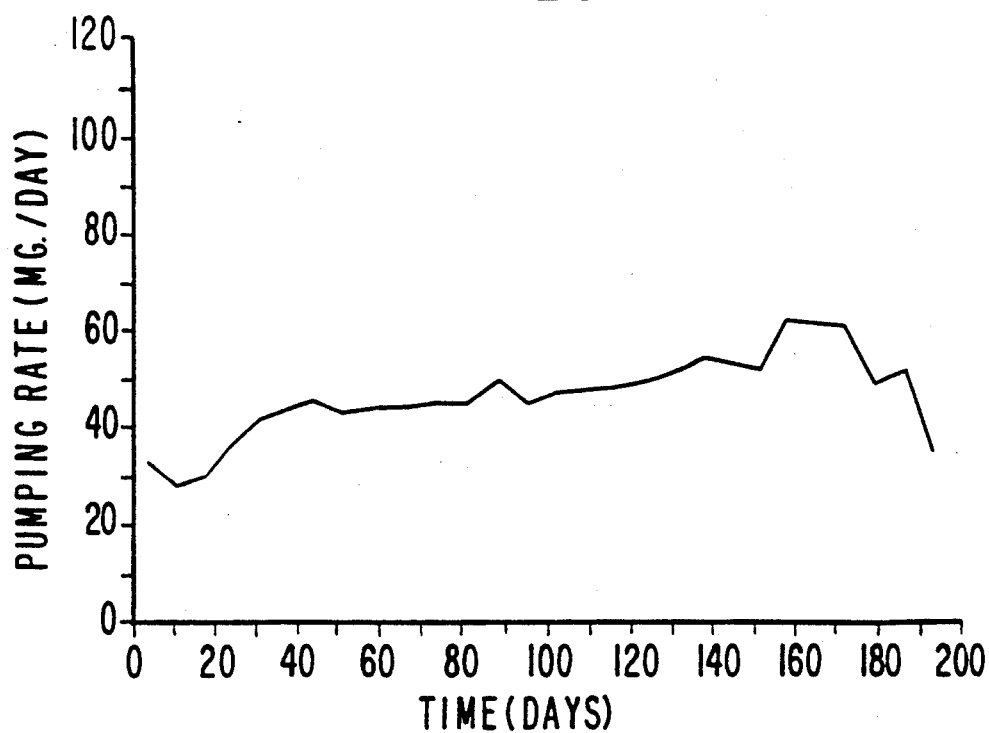
Figure 21:
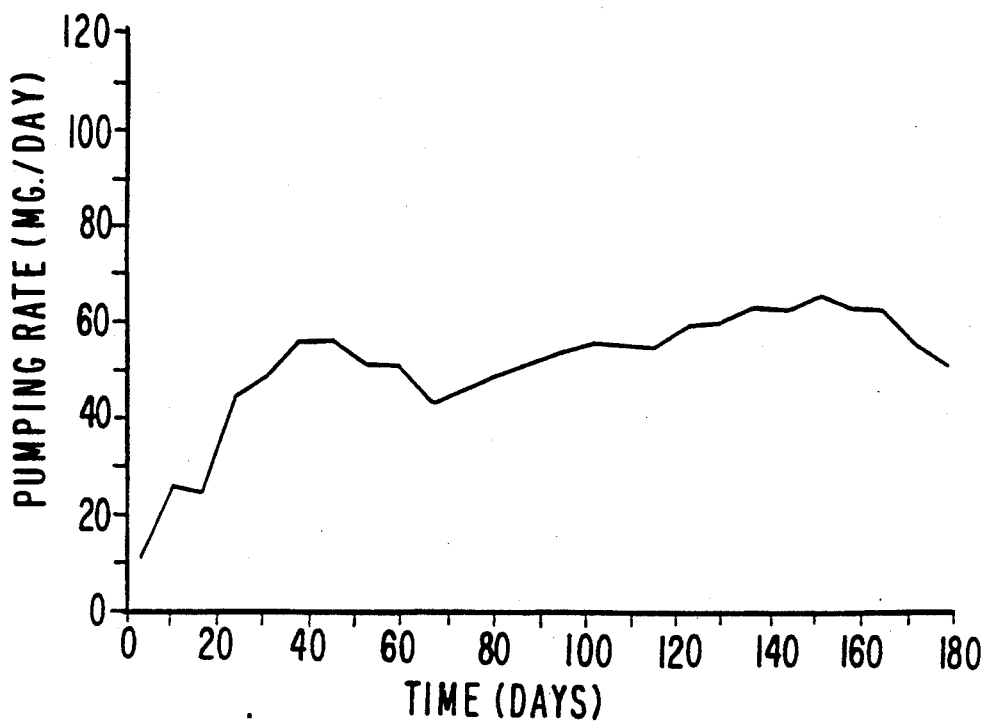
Figure 22:
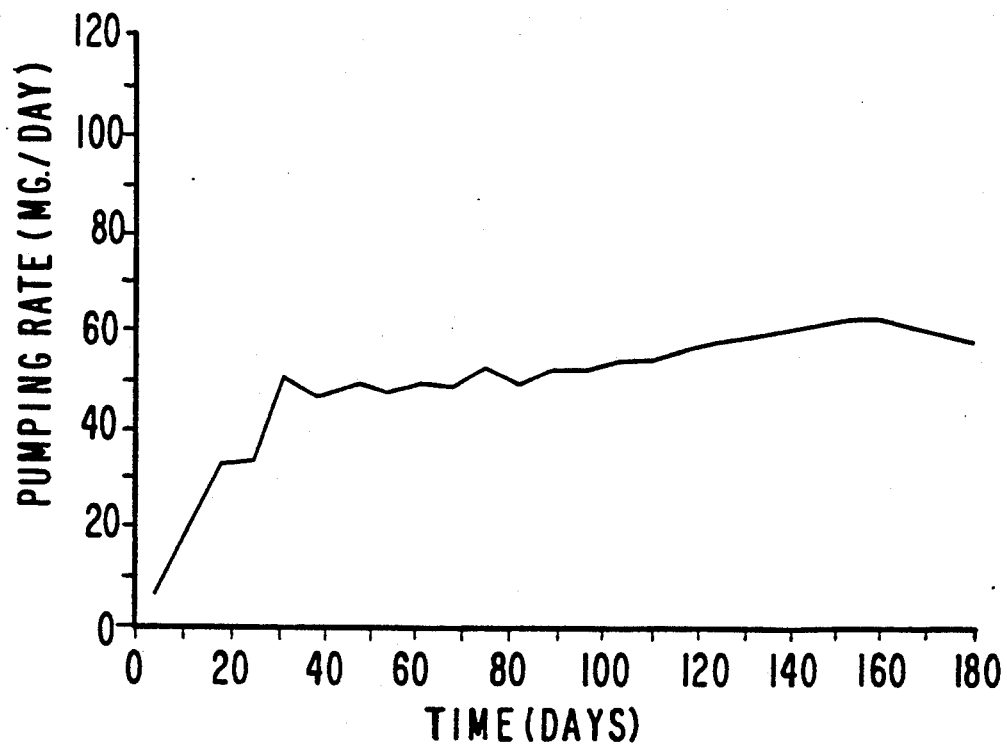

17 depicts the release rate patterns from a delivery system comprising a drug load of 15% ivermectin and a 0.150 inch bore through the density member as measured in artificial ruminal fluid containing 75% carbon dioxide; drawing FIG. 18 depicts the release rate pattern from a delivery system comprising a 15% drug load of ivermectin, a 0.200 inch bore through the density member covered with a mesh screen and measured in artificial ruminal fluid containing 75% carbon dioxide; drawing FIG. 19 depicts the release rate profile from a delivery system comprising a 15% load of ivermectin, 2% silicon dioxide, a 0.150 inch bore and measured in artificial ruminal fluid containing 75% carbon dioxide; drawing FIG. 20 depicts the release rate pattern from a delivery system comprising 15% ivermectin, a 0.200 inch bore covered by a mesh screen and measured in vivo; drawing FIG. 21 depicts the release rate pattern from a delivery device comprising 15% ivermectin, 2% silicon dioxide, a 0.200 inch bore covered with a pressure inducing screen and measured in artificial ruminal fluid comprising 75% carbon dioxide; drawing, FIG. 22 depicts the release rate pattern from a delivery system comprising a 15% drug load, 2% of silicon dioxide, a 0.200 inch bore with a screen and the measurements made in vivo. Accompanying FIGS. 18 to 22 all represent improvements over the release rate profile of FIG. 17.

DISCLOSURE OF METHOD OF USING THE INVENTION

An embodiment of the invention pertains to a method for administering to a warm blooded animal a beneficial drug at a controlled rate and in a presently preferred method to the rumen of a ruminant, which method comprises the steps of: (A) admitting orally into an animal such as the rumen of a ruminant in need of a beneficial drug an improved dispensing device comprising: (1) a wall comprising in at least a part a semipermeable polymeric composition permeable to the passage of fluid and substantially impermeable to the passage of drug, the wall surrounding; (2) an internal lumen comprising a layer thermo-responsive composition comprising a dosage unit amount of a beneficial drug, said thermo-responsive composition softening and forming at animal body temperature a dispensable formulation that is a means for transporting the drug from the dispenser, said thermo-responsive composition optionally including a physiologically inert agent or compound that increases the viscosity and/or yield stress of the thermo-responsive composition; (3) a layer of a push composition in the lumen for displacing the thermo-responsive composition from the dispenser; (4) an optional layer of a dense member for keeping the dispenser when in a rumen over a prolonged period of time; and (5) (a) an improvement in an exit member for increasing the pressure in the device and for increasing the hydraulic resistance to flow in the wall communicating with the lumen, and, (b) an improvement in the thermo-responsive composition comprising means for increasing the viscosity and/or yield stress of the thermo-responsive composition; (B) imbibing fluid through the semipermeable wall at a rate determined by the permeability of the semipermeable wall and the osmotic pressure gradient across the semipermeable wall to cause push composition to increase in volume; (C) softening the thermo-responsive composition to form a dispensable flowable formulation; and (D) delivering the beneficial drug from the dispenser by the push composition continually displacing the dispensable formulation through the exit member in a therapeutically effective amount at a controlled, consistent and predictable rate to the rumen over a prolonged period of time from 1 day to 350 days.

Inasmuch as the foregoing specification comprises preferred embodiments of the invention, it is understood that variations and modifications may be made herein in accordance with the inventive principles disclosed, without departing from the scope of the invention.

We claim:

1. A process for increasing the internal pressure of a dispenser, wherein the dispenser comprises:
   i) a wall that surrounds a lumen,
   ii) a thermo-responsive composition in the lumen,
   iii) a beneficial agent mixed with the thermo-responsive composition,
   iv) optionally, a density member in the lumen for increasing the weight of the dispenser,
   v) push means in the lumen for displacing the thermo-responsive composition from the dispenser, and
   vi) an exit opening in the wall that communicates with the lumen;

wherein, the process comprises:
   a) mixing a viscosity-inducing amount of an inert viscosity-inducing agent into the thermo-responsive composition for increasing the viscosity of the thermo-responsive composition, and
   b) positioning a pressure-inducing exit member in the exit opening in the wall of the dispense, whereby steps a) and b) increase the internal pressure of the dispenser.

2. A process for increasing the internal pressure of a dispenser according to claim 1 wherein the viscosity-inducing agent is silicon dioxide.

3. A process for increasing the internal pressure of a dispenser according to claim 1 wherein the viscosity-inducing agent is selected from the group consisting of silica, sand, precipitated silica, amorphous silica, colloidal silicon dioxide, fused silica, quartz, silica gel, and a siliceous composition.

4. A process for increasing the internal pressure of a dispenser according to claim 1 wherein the process comprises positioning a releaseable pressure-inducing exit member in the exit opening in the wall.

5. A process for increasing the internal pressure of a dispenser according to claim 1 wherein the exit member is an insert for placement in the exit opening in the wall of the dispenser.

6. A process for increasing the internal pressure of a dispenser according to claim 1 wherein the exit member is selected from a grid, a perforated plate, a plurality of capillaries, and a plurality of tubes.

7. A process for increasing the internal pressure of a dispenser according to claim 5 wherein the exit member is selected from a grid, a perforated plate, a plurality of capillaries, and a plurality of tubes.

8. A process for increasing the internal pressure of a dispenser according to claim 1 wherein the beneficial agent is avermectin or ivermectin.

9. A process for increasing the internal pressure of a dispenser according to claim 1 wherein the push means comprises an osmagent, an osmopolymer or an osmagnet together with an osmopolymer.

10. A process for increasing the internal pressure of a dispenser according to claim 1 wherein the dispenser further comprises an inert partition in the lumen between the thermo-responsive composition and the push means.

11. A process for increasing the internal pressure of a dispenser according to claim 1 wherein the density member comprises a weight with a bore in the weight, and the exit member is in contact with the bore.

12. A process for increasing the internal pressure of a dispenser, wherein the dispenser comprises:
   i) a wall that surrounds a lumen,
   ii) a thermo-responsive composition in the lumen,
   iii) a beneficial agent mixed with the thermo-responsive composition,
   iv) optionally, a density member in the lumen for increasing the weight of the dispenser,
   v) push means in the lumen for displacing the thermo-responsive composition from the dispenser, and
   vi) an exit opening in the wall that communicates with the lumen;
   wherein, the process comprises;
      a) mixing a viscosity-inducing amount of an inert viscosity-inducing agent into the thermo-responsive composition for increasing the viscosity of the thermo-responsive composition to increase the internal pressure of the dispenser.

13. A process for increasing the internal pressure of a dispenser according to claim 12 wherein the viscosity-inducing agent is silicon dioxide.

14. A process for increasing the internal pressure of a dispenser according to claim 12 wherein the viscosity-inducing agent is selected from the group consisting of silica, sand, precipitated silica, amorphous silica, colloidal silicon dioxide, fused silica, quartz, silica gel, and a siliceous composition.

15. A process for increasing the internal pressure of a dispenser according to claim 12 wherein the viscosity-inducing agent increases the stress to flow of the thermo-responsive composition.

16. A process for increasing the internal pressure of a dispenser, wherein the dispenser comprises:
   i) a wall that surrounds a lumen,
   ii) a thermo-responsive composition in the lumen,
   iii) a beneficial agent mixed with the thermo-responsive composition,
   iv) optionally, a density member in the lumen for increasing the weight of the dispenser,
   v) push means in the lumen for displacing the thermo-responsive composition from the dispenser, and
   vi) an exit opening in the wall that communicates with the lumen;
   wherein, the process comprises:
      a) positioning a pressure-inducing exit member in the exit opening in the wall of the dispenser to increase the internal pressure of the dispenser.

17. A process for increasing the internal pressure of a dispenser according to claim 16 wherein the process comprises positioning a releasable pressure-inducing exit member in the exit opening in the wall.

18. A process for increasing the internal pressure of a dispenser according to claim 16 wherein the exit member is an insert for placement in the exit opening in the wall of the dispenser.

19. A process for increasing the internal pressure of a dispenser according to claim 16 wherein the exit member is selected from a grid, a perforated plate, a plurality of capillaries, and a plurality of tubes.

20. A process for increasing the internal pressure of a dispenser according to claim 18 wherein the exit member is selected from a grid, a perforated plate, a plurality of capillaries, and a plurality of tubes.

* * * * *